(12) United States Patent
Bonin et al.

(10) Patent No.: US 10,481,153 B2
(45) Date of Patent: Nov. 19, 2019

(54) INTEGRATED COMPOUND DISCOVERY SYSTEMS AND METHODS

(71) Applicants: Wake Forest University, Winston-Salem, NC (US); NanoMedica LLC, Winston-Salem, NC (US)

(72) Inventors: Keith Bonin, Winston-Salem, NC (US); Jed C. Macosko, Winston-Salem, NC (US); Jason Gagliano, Tobaccoville, NC (US); Martin Guthold, Pfafftown, NC (US); Roger Cubicciotti, Winston-Salem, NC (US)

(73) Assignees: Wake Forest University, Winston-Salem, NC (US); NanoMedica LLC, Winston-Salem, NC (US)

( * ) Notice: Subject to any disclaimer, the term of this patent is extended or adjusted under 35 U.S.C. 154(b) by 28 days.

(21) Appl. No.: 15/654,309

(22) Filed: Jul. 19, 2017

(65) Prior Publication Data

US 2017/0322206 A1    Nov. 9, 2017

Related U.S. Application Data

(62) Division of application No. 14/346,362, filed as application No. PCT/US2012/071258 on Dec. 21, 2012, now Pat. No. 9,746,466.

(60) Provisional application No. 61/579,842, filed on Dec. 23, 2011.

(51) Int. Cl.
*G01N 33/543* (2006.01)
*C12Q 1/6837* (2018.01)

(52) U.S. Cl.
CPC ..... *G01N 33/54353* (2013.01); *C12Q 1/6837* (2013.01); *C12Q 2565/514* (2013.01); *C12Q 2600/136* (2013.01); *G01N 2500/04* (2013.01); *G01N 2500/20* (2013.01)

(58) Field of Classification Search
CPC .......................... G01N 33/54353; C12Q 1/6837
See application file for complete search history.

(56) References Cited

U.S. PATENT DOCUMENTS

| 6,287,765 | B1 | 9/2001 | Cubicciotti et al. |
| 6,391,562 | B2 | 5/2002 | Kambara et al. |
| 6,573,089 | B1 | 6/2003 | Vann |
| 7,320,864 | B2 | 1/2008 | Yang |
| 8,048,627 | B2 | 11/2011 | Dressman et al. |
| 8,741,558 | B2 | 6/2014 | Guthold et al. |
| 2002/0164611 | A1 | 11/2002 | Bamdad et al. |
| 2003/0082587 | A1 | 5/2003 | Seul et al. |
| 2003/0228619 | A1 | 12/2003 | Needels |
| 2005/0123939 | A1 | 6/2005 | Gorenstein et al. |
| 2006/0292559 | A1 | 12/2006 | Reddy et al. |
| 2007/0065823 | A1 | 3/2007 | Dressman et al. |
| 2008/0200340 | A1 | 8/2008 | Gorenstein et al. |
| 2008/0242555 | A1 | 10/2008 | Shen et al. |
| 2008/0255005 | A1 | 10/2008 | Gorenstein et al. |
| 2009/0017022 | A1 | 1/2009 | Naworth et al. |
| 2009/0017455 | A1 | 1/2009 | Kwong et al. |
| 2009/0123922 | A1 | 5/2009 | Gorenstein et al. |
| 2010/0282617 | A1 | 11/2010 | Rothberg et al. |

FOREIGN PATENT DOCUMENTS

| WO | WO 99/45149 A1 | 9/1999 |
| WO | WO 02/099078 | * 12/2002 |
| WO | WO 2008/076406 A2 | 6/2008 |
| WO | WO 2010/091144 A1 | 8/2010 |

OTHER PUBLICATIONS

Braslavsky et al. "Sequence information can be obtained from single DNA molecules" *PNAS* 100(7):3960-3964 (2003).
Cockroft et al. "A single-molecule nanopore device detects CAN polymerase activity with single-nucleotide resolution" *J Am Chem Soc.* 130(3):818-820 (2008).
Dressman et al. "Transforming single DNA molecules into fluorescent magnetic particles for detection and enumeration of genetic variations" *PNAS* 100(15):8817-8822 (2003).
Gassman et al. "Selection of bead-displayed, PNA-encoded chemicals" *Journal of Molecular Recognition* 23(5):414-421(2010).
International Search Report and Written Opinion corresponding to International Patent Application No. PCT/US2010/023141 (dated Apr. 22, 2010).
International Search Report and Written Opinion corresponding to International Patent Application No. PCT/US2012/071258 (dated Jun. 20, 2013).
Jeong et al. "Rewritable remote encoding and decoding of miniature multi-bit magnetic tags for high-throughput biological analysis" *Lab on a Chip* 8(11):1883-1887 (2008).
Kinoshita et al. "Novel concept microarray enabling PCR and multistep reactions through pipette-free aperture-to-aperture parallel transfer" *BMC Biotechnology* 10(71):1-16 (2010).

(Continued)

*Primary Examiner* — Narayan K Bhat
(74) *Attorney, Agent, or Firm* — Myers Bigel, P.A.

(57) ABSTRACT

Methods, systems, devices and apparatus for use in screening and/or selecting a library of nucleic acid molecules and/or nucleic acid tagged or encoded molecules for binding to or interaction with a target molecule or substance (e.g., for use in new compound or drug discovery) are described. In some embodiments the device comprises: (a) a spatially addressable array, said array comprising a plurality of separate and discrete locations thereon; (b) a plurality of different oligomers operably connected to said spatially addressable array at different ones of said separate and discrete locations; (c) a tag sequence which is complementary to, and is hybridized to, each of said oligomers; and (d) a candidate chemical operably connected to each of said tag sequences, wherein each of said discrete locations is a unique identifier for its corresponding oligomer; and wherein said tag sequence is a unique identifier for its connected candidate chemical.

16 Claims, 9 Drawing Sheets

Specification includes a Sequence Listing.

(56) References Cited

Kleiner et al. "In vivo selection of a DNA-templated small-molecule library reveals a class of macrocyclic kinase inhibitors" *J Am Chem Soc.* 132:11779-11791 (2010).
Liu et al. "Evolutionary principles applied to the discovery and study of functional biological and synthetic molecules" *Liu Group Research Summary* (10 pages) (2006).
Ma et al. "Chemical microarray: a new tool for drug screening and discovery" *Drug Discovery Today* 11(13/14):661-668 (2006).
Mannocci et al. "High-throughput sequencing allows the identification of binding molecules isolated from DNA-encoded chemical libraries" *PNAS* 105(46):17670-17675 (2008).
Peng et al. "A combined atomic force/fluorescence microscopy technique to select aptamers in a single cycle from a small pool of random oligonucleotides" *Microscopy Research and Technique* 70:372-381 (2007).
Pushkarev et al. "Single-molecule sequencing of an individual human genome" *Nature Biotechnology* 27(9):847-852 (2009).
Rothberg et al. "Integrated semiconductor device enabling non-optical genome sequencing" *Nature* 475:348-352 (2011).
Stoddart et al. "Single-nucleotide discrimination in immobilized DNA oligonucleotides with a biological nanopore" *PNAS* 106(19):7702-7707 (2009).
Yang et al. "Construction and selection of bead-bound combinatorial oligonucleoside phosphorothioate and phosphorodithioate aptamer libraries designed for rapid PCR-based sequencing" *Nucleic Acids Research* 30(23):e132 (2002).
Nutiu et al. "Direct visualization of DNA affinity landscapes using a high-throughput sequencing instrument" Nature Biotechnology, 29(7):659-664 (2012).

* cited by examiner

INTEGRATED COMPOUND DISCOVERY SYSTEMS AND METHODS

RELATED APPLICATIONS

This application is a divisional application of U.S. patent application Ser. No. 14/346,362, filed Mar. 21, 2014, which is a 35 U.S.C. § 371 national phase entry of PCT Application PCT/US2012/071258, filed Dec. 21, 2012, and published in English on Jun. 27, 2013, as International Publication No. WO 2013/09677, and which claims the benefit of U.S. Provisional Patent Application Ser. No. 61/579,842, filed Dec. 23, 2011, the disclosure of each of which is incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 9151-177TSDV_ST25.txt, 684 bytes in size, generated on Jul. 19, 2017 and filed via EFS-Web, is provided in lieu of a paper copy. This Sequence Listing is hereby incorporated by reference into the specification for its disclosures.

FIELD OF THE INVENTION

The present invention concerns compositions, methods, devices and apparatus for use in screening and/or selecting a library of nucleic acid molecules and/or nucleic acid tagged or encoded molecules for binding to or interaction with a target molecule or substance.

BACKGROUND OF THE INVENTION

Pharmaceutical product pipelines and FDA approval rates have weakened dramatically over the past decade. In addition, with recently accelerating discovery of new diagnostic analytes, biomarkers and targets of clinical and industrial interest, there is a growing need for new analytical and clinical reagents and molecular probes. To aid in the discovery of new drug candidate, diagnostic reagents and industrially useful target-binding ligands, the bead-based screening technology described by Drs. Guthold and Macosko (PCT Patent Application WO 2010/091144, published Aug. 12, 2010) was developed. One limitation of the technology described therein is the need for a "pick-up" step (e.g., atomic-force microscopy or micropipette-based bead pick-up) in combination with subsequent sequencing steps, for identification of candidate compounds. While this limitation can potentially be addressed through automation and microminiaturization, there is a need for new, more rapid and cost-effective compound discovery systems and methods to screen, select and identify new and useful ligands, probes and effector molecules.

SUMMARY OF THE INVENTION

A first aspect of the invention is a device comprising:
(a) a spatially addressable array, said array comprising a plurality of separate and discrete locations thereon;
(b) a plurality of different oligomers operably connected to said spatially addressable array at different ones (including but not limited to predetermined ones) of said separate and discrete locations;
(c) a tag sequence which is complementary to, and is hybridized to, each of said oligomers; and
(d) a candidate chemical operably connected to each of said tag sequences,
wherein each of said discrete locations is a unique identifier for its corresponding oligomer;
and wherein said tag sequence is a unique identifier for its connected candidate chemical.

In some embodiments of the foregoing, the spatially addressable array is a field-effect transistor array, an electrochemical array or an optical array.

In some embodiments of the foregoing, the oligomers and said tag sequences are nucleic acids.

In some embodiments of the foregoing, the said candidate chemicals are selected from the group consisting of small molecules, peptides, carbohydrates, lipids, monomers, polymers and conjugated molecules.

In some embodiments of the foregoing, the array comprises a substrate having a plurality of wells formed therein, said wells defining said plurality of separate and discrete locations; said device further comprising at least one particle deposited in each well of at least a subset of said plurality of wells, with said oligomers coupled to said particles.

A further aspect of the invention is a method for identifying a candidate molecule from a library of candidate chemicals, which comprises the steps of:
(a) detecting or probing a target molecule with a device comprising:
  (i) a spatially addressable array, said array comprising a plurality of separate and discrete locations thereon;
  (ii) a plurality of different oligomers operably connected to said spatially addressable array at different ones (including but not limited to predetermined ones) of said separate and discrete locations;
  (iii) a tag sequence which is complementary to, and is hybridized to, each of said oligomers; and
  (iv) a candidate chemical operably connected to each of said tag sequences,
  wherein each of said discrete locations is a unique identifier for its corresponding oligomer;
  and wherein said tag sequence is a unique identifier for its connected candidate chemical;
(b) identifying each of said separate and discrete locations to which said target molecule is bound; and then
(c) identifying, from a database correlating each of said separate and discrete locations with its connected candidate chemical, the candidate molecule.

In some embodiments of the foregoing, the target molecule comprises at least one of a protein, a peptide, a therapeutic target or a diagnostic analyte.

In some embodiments of the foregoing, the array comprises a substrate having a plurality of wells formed therein, said wells defining said plurality of separate and discrete locations; said device further comprising at least one particle deposited in each well of at least a subset of said plurality of wells, with said oligomers coupled to said particles.

In some embodiments of the foregoing, the candidate molecule comprises a nucleic acid aptamer;

Some embodiments of the foregoing further comprise the step of: (d) quantitatively determining at least one binding property of said candidate chemical to said target molecule, wherein said binding property includes at least one of signal intensity, signal duration, dissociation kinetics, association kinetics, target-binding specificity or binding-dependent modulation of target molecule activity.

A further aspect of the invention is a device comprising:
(a) a spatially addressable array, said array comprising a plurality of separate and discrete locations thereon;

(b) a plurality of different oligomers operably connected to said spatially addressable array at different predetermined ones of said separate and discrete locations;

(c) a nonnucleic acid target molecule noncovalently bound to at least one of said different oligomers.

In some embodiments of the foregoing, the nonnucleic acid target molecule comprises at least one of a protein, a peptide, a therapeutic target or a diagnostic analyte.

In some embodiments of the foregoing, the spatially addressable array is a field effect transistor array, an electrochemical array or an optical array.

In some embodiments of the foregoing, the oligomers are nucleic acids.

In some embodiments of the foregoing, the oligomers are selected from the group consisting of nucleotides, oligonucleotides and nonnaturally occurring nucleic acid molecules.

In some embodiments of the foregoing, the oligomers further comprise at least one of a tag sequence or a nonnucleic acid moiety.

In some embodiments of the foregoing, the array comprises a substrate having a plurality of wells formed therein, said wells defining said plurality of separate and discrete locations; said device further comprising at least one particle deposited in each well of at least a subset of said plurality of wells, with said oligomers coupled to said particles.

A further aspect of the invention is a method for identifying a candidate molecule from a library of candidate oligomer molecules, which comprises the steps of:

(a) detecting or probing at least one candidate oligomer that binds to a target molecule with a device comprising:
  (i) a spatially addressable array, said array comprising a plurality of separate and discrete locations thereon;
  (ii) a plurality of different candidate oligomers operably connected to said spatially addressable array at different ones (including but not limited to predetermined ones) of said separate and discrete locations; and (b) determining the sequence of all or part of the at least one candidate oligomer operably attached to at least one of said separate and discrete locations to which said target molecule binds.

In some embodiments of the foregoing, the target molecule comprises a protein, a peptide, a therapeutic target or a diagnostic analyte.

In some embodiments of the foregoing, the array comprises a substrate having a plurality of wells formed therein, said wells defining said plurality of separate and discrete locations; said device further comprising at least one particle deposited in each well of at least a subset of said plurality of wells, with said oligomers coupled to said particles.

A further aspect of the invention is a sequencing-based molecular discovery system comprising:

(a) input apparatus as a means for inputting input reagents including at least:
  (i) a library of nucleotide-based or nucleotide-encoded candidate chemicals,
  (ii) a nonnucleic acid target molecule; and
  (iii) nucleic acid sequencing reagents;

(b) a sequencing device operatively associated with said input apparatus or means for inputting and comprising a spatially addressable array, said array comprising a plurality of separate and discrete locations thereon;

(c) a reading apparatus or other suitable means, operatively associated with said sequencing device, for determining the sequence of a nucleotide-based or nucleotide-encoded candidate chemical disposed on at least one of said separate and discrete locations; and (d) a binding detector or means, operatively associated with said sequencing apparatus or means or device, for detecting the binding of the nonnucleic acid target molecule to said nucleotide-based or nucleotide-encoded candidate chemical disposed on the at least one separate and discrete location.

In some embodiments, the input apparatus or means for inputting input reagents comprises: a single sample introduction port; a library supply or reservoir(s) operatively associated with said port; a nonnucleic acid target molecule supply or reservoir(s) operatively associated with said port; and a sequencing reagent supply or reservoir(s) operatively associated with said port. All may be operatively associated to the port through tubing, piping, valves, which may be operated manually or under the control of a suitable controller.

In some embodiments, the reader or means for determining the sequence of the nucleotide-based or nucleotide-encoded candidate chemical comprises at least one of an optical, electromagnetic, electrical, or electrochemical detection apparatus. In some embodiments, the detection apparatus comprises a bead-, polony-, well- or site-based sequencing apparatus configured for disposing said candidate chemicals in or on said beads, polonies, wells or sites.

In some embodiments, the binding detector or means for detecting the binding of said nonnucleic acid target molecule to said nucleotide-based or nucleotide-encoded candidate chemical comprises at least one of directly labeled target molecules, secondary labeling reagents, labeled anti-target antibodies, peptides or ligands and structural or functional assay of target properties, activities, structure or function in bound versus unbound states. For example, the binding detector may, in some embodiments, comprise a microscope, an image detector, an optical detector, a radiation detector, or other suitable detector, examples of which include, but are not limited to, a fluorescence microscope, an electron microscope, an optical microscope, an absorbance-based microscope, a photon detection system, an acoustic detection system, a surface plasmon resonance detection system, a thermal detection system, an electromagnetic detection system, a waveguide, a CCD camera, a confocal microscope, a laser-scanning device, a fluidic and/or mechanical detection system, an isotopic detection system, and elemental analysis, including, e.g., x-ray scattering, etc., including combinations thereof.

The present invention is explained in greater detail in the drawings herein and the specification set forth below, which set forth non-limiting examples, illustrations, and embodiments of the invention. The disclosures of all US Patent references cited herein are to be incorporated herein by reference in their entirety.

Figure 1:
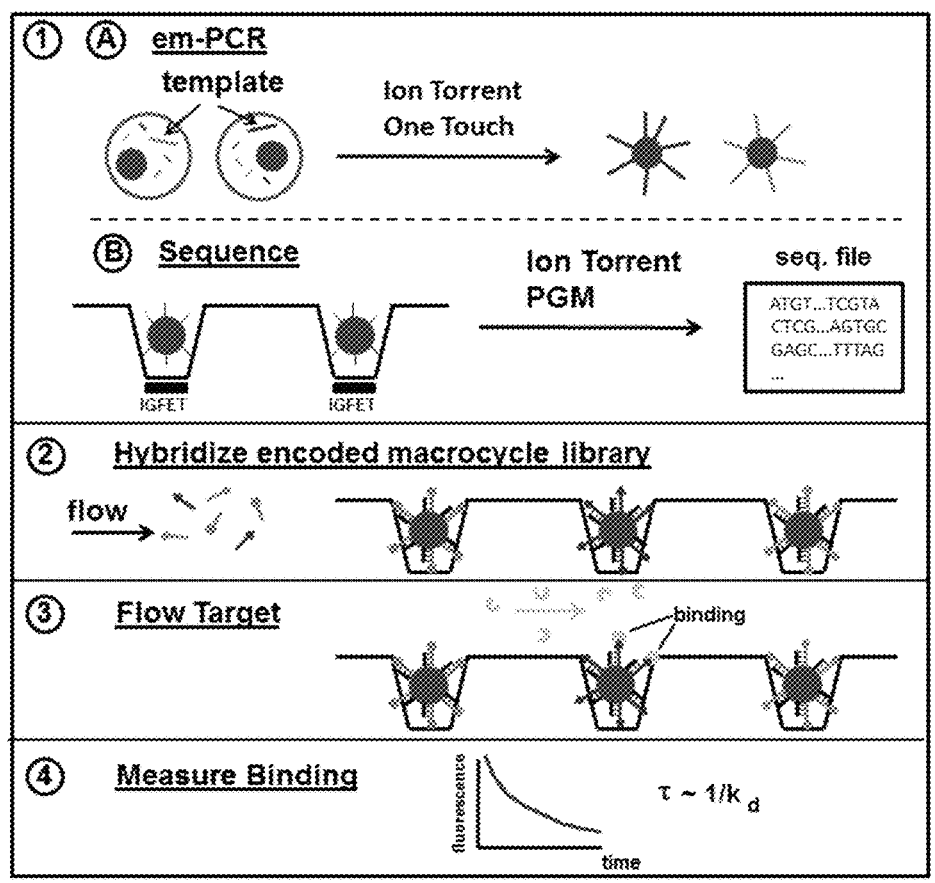
FIG. 1. Schematic of steps involved in one embodiment of the invention. In step 1, beads (each bead becomes decorated with multiple copies of a single nucleic acid sequence via em-PCR as show in step 1A) are placed in spatially addressable wells and sequenced by a next-generation sequencer as shown in step 1B (Ion Torrent PGM). In step 2, the compound library (lollipop-shaped objects) flows in and attaches to the beads in wells (one compound, or macrocycle, per bead/well). In step 3 a target flows past beads with compounds, and target-binders are detected in step 4 (optically, e.g., through fluorescence). Target binding to a candidate macrocycle from a nucleic acid-encoded macrocycle library is detected on single nucleic acid-modified beads that have been previously sequenced by Ion Torrent Sequencing (ITS) (one of the growing number of sequencing systems that provides the spatially addressable location and sequence of each member of a nucleic acid library). Thus, the identity of each compound is known immediately, without the need for iterative selection cycles or subcloning. The lifetime, an estimate of binding affinity, of each compound-target pair can be determined on-chip which is a significant benefit over offline assay techniques that require extraction, processing and analysis.

Basically, steps 2A and 3A represent essentially the same macrocycle selection process illustrated in FIG. 1. Steps 2B and 3B represent an alternative process through which nucleic acid aptamers, rather than nucleotide-encoded macrocycles, are selected for desired target-binding properties. Step 2B shows aptamer candidates from a nucleic acid-bead library disposed in wells of an ITS chip. In step 3B a target molecule (same or different as step 3A) is flowed in to bind target-specific aptamers.

Figure 3:
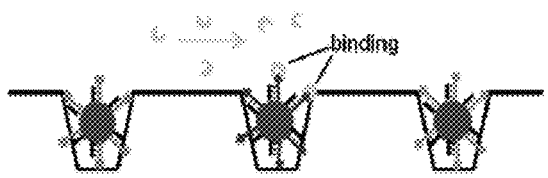
Figure 3:
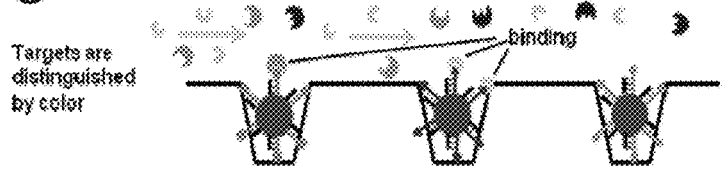
Figure 3:
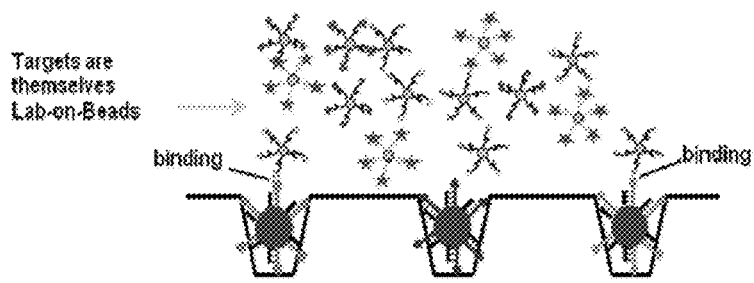

FIG. 3. Schematic of step 3 showing (in 3 panels) the powerful ability to multiplex target binding by flowing more than one target candidate simultaneously to measure target binding to small molecules or aptamers. Steps 1, 2, and 4 are similar to FIG. 1 above. Here, panels 2 & 3 show multiple different targets being used (multiplexing). Panel 3 shows a specific case where the target molecules are themselves "Lab-on-Bead" constructs as described in Guthold and Macosko, PCT Patent Application WO 2010/091144, published Aug. 12, 2010. Such a construct might to be used, for example, with targets consisting of proteins attached to mRNA In a related embodiment, multiple copies of each of the different target molecules are attached to a bead or alternative carrier in a single target species per bead configuration. In this configuration, the bead-target constructs may comprise nucleic acid or nucleotide-encoded molecules that are optionally hybridized to bead-immobilized nucleic acid molecules in the same manner as single sequence-per-bead libraries described elsewhere herein, Thus, a first library of single-sequence-per-bead nucleic acid or nucleotide-encoded molecules (e.g., a DNA-encoded macrocycle library) may serve as a library of candidate target-binding molecules and a second library of single-sequence-per-bead nucleic acid or nucleotide-encoded molecules (e.g., a PNA-encoded library) may serve as a library of candidate target molecules.

Figure 4:
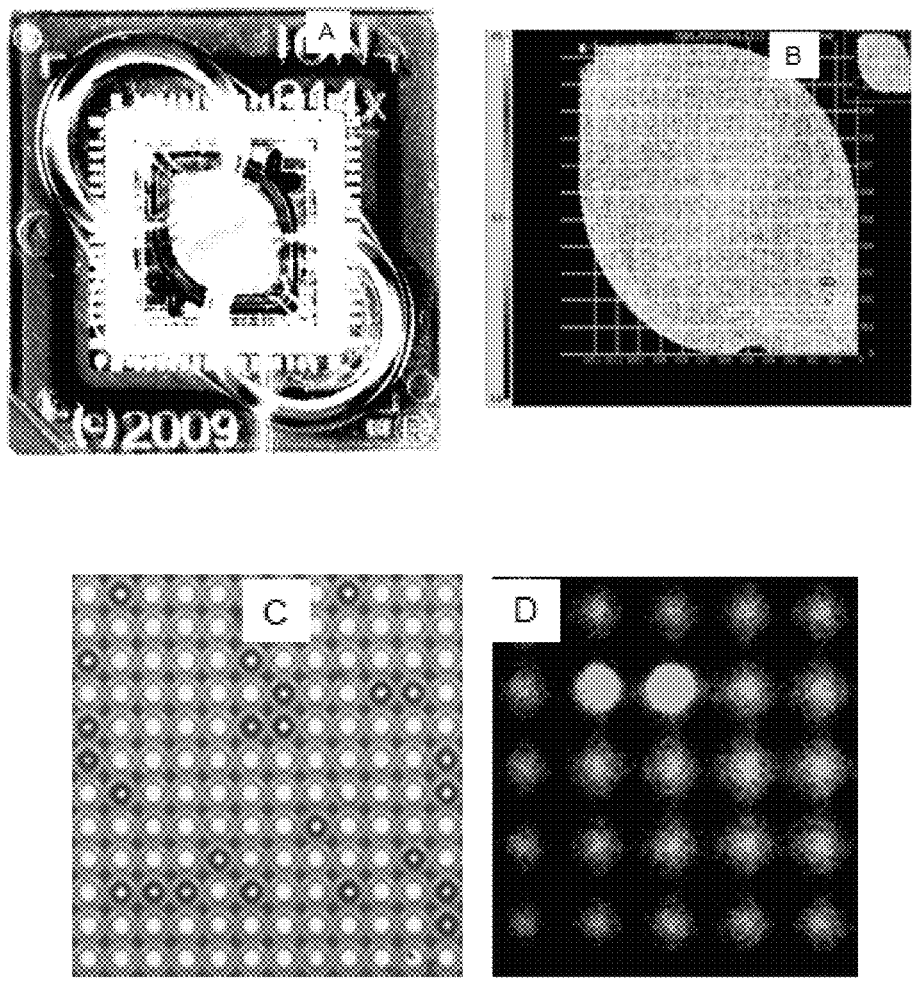

FIG. 4. (A) Ion Torrent 314 chip. The eye-shaped structure in the center of the white square contains 1.3 million sequencing wells. The inlet and outlet slots for the sample are in the center of the two large circular shapes that can be seen at two corners of the white square; chip size, ~1 inch. (B) Image of Ion Torrent chip with superimposed sequence read scores for each of the 1.3 million wells (white—acceptable; black—rejected). (C) Brightfield image of the Ion Torrent 314 chip after sequencing; dark circles indicate a well filled with a bead; bright disks, empty wells. (D) Fluorescence image of two fluorescent magnetic beads (larger white disks) located among the nonfluorescent Ion Torrent beads (smaller white smudges). (Well size: 3 um in all images).

Figure 5:
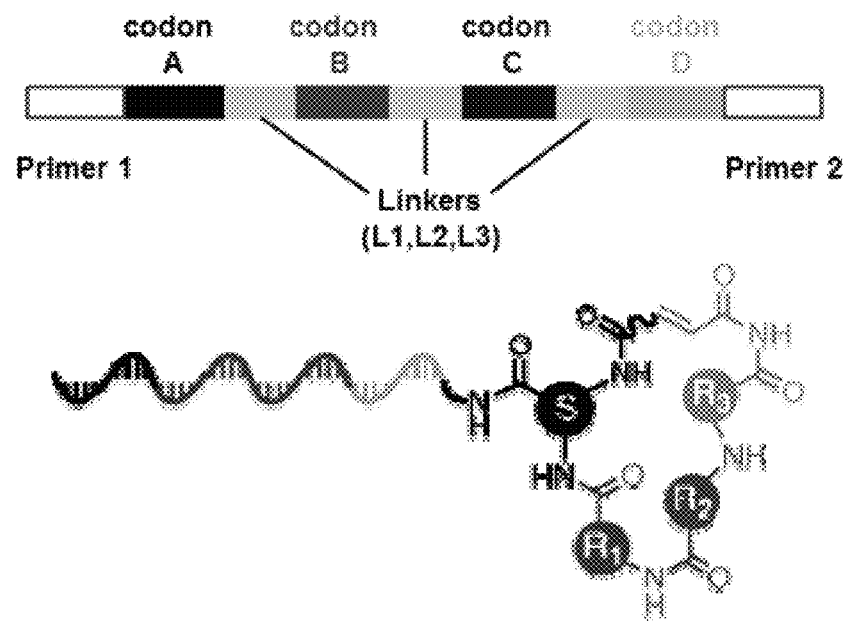

FIG. 5. (A) Schematic DNA template, in which the codons are sequences that code for a particular chemical group. (B) Encoded macrocycle (DNA-tagged macrocycle), consisting of four chemical groups, S, $R_1$, $R_2$, $R_3$.

Figure 2:
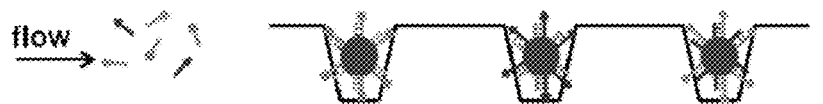
FIG. 2. Schematic of steps 2-3 originally detailed in FIG. 1 showing two alternative embodiments of the invention. Steps 1 and 4 are similar to FIG. 1 above. Here, in step 2, two types of compound libraries are shown: (a) a library of tagged small molecules and (b) a library of nucleic acid-based aptamer candidates, the sequences of which serve as their own tag (identifier). In step 3 we show a target flowing into the sequencing device and binding to (a) one of the small molecules in the first library and/or (b) one of the aptamers in the second.
Figure 2:
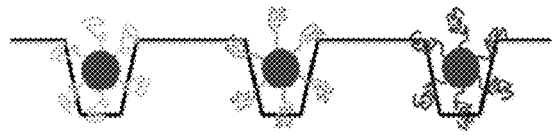
Figure 2:
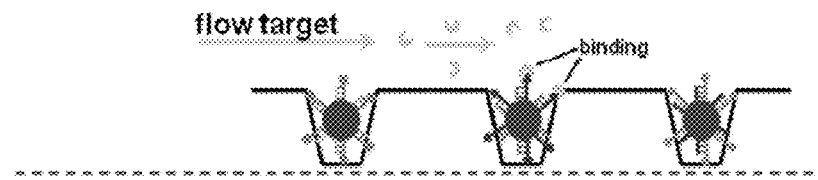
Figure 2:
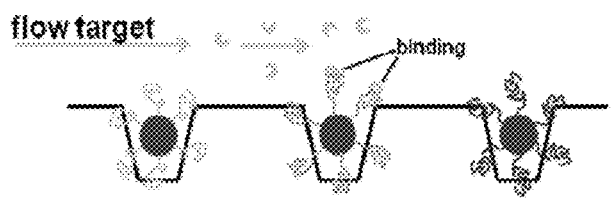
Figure 6:
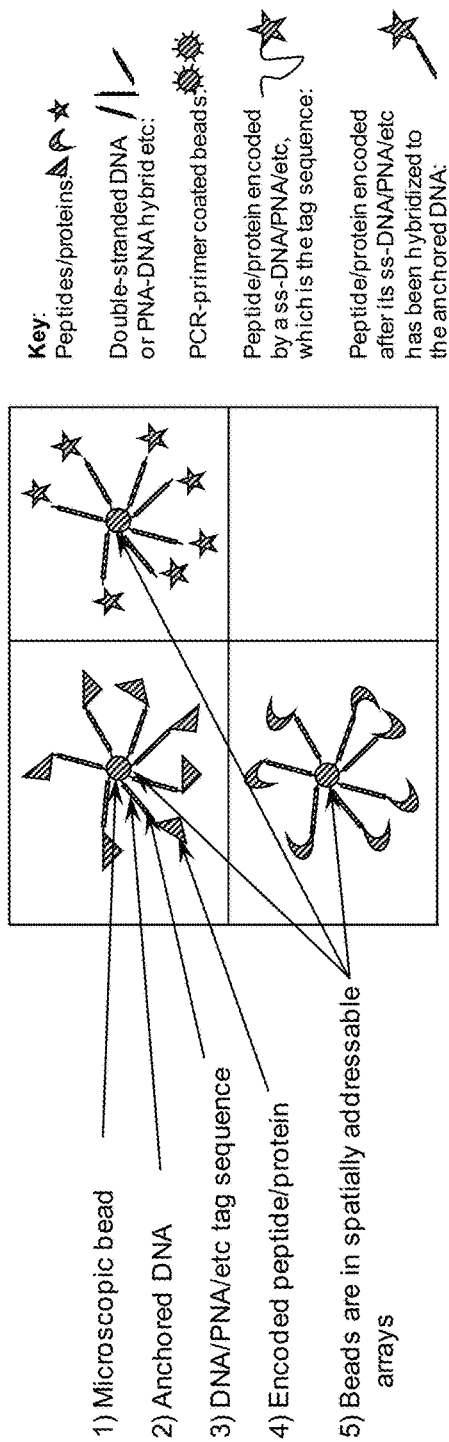

FIG. 6. Schematic illustrating components of bead-based arrays for sequencing and identifying target-binding candidate chemicals. This schematic shows a top-down view that is different from the side views shown in FIGS. 1-3. In this schematic, every bead contains multiple copies of one unique sequence; each bead has a different sequence. Another difference between this figure and FIGS. 1-3 is that these unique sequences encoded peptide or protein instead of encoded chemicals like macrocycles. The capturing is still such that each bead displays multiple copies of only one type of molecule (in this case peptide or protein rather than small chemicals).

Figure 7:
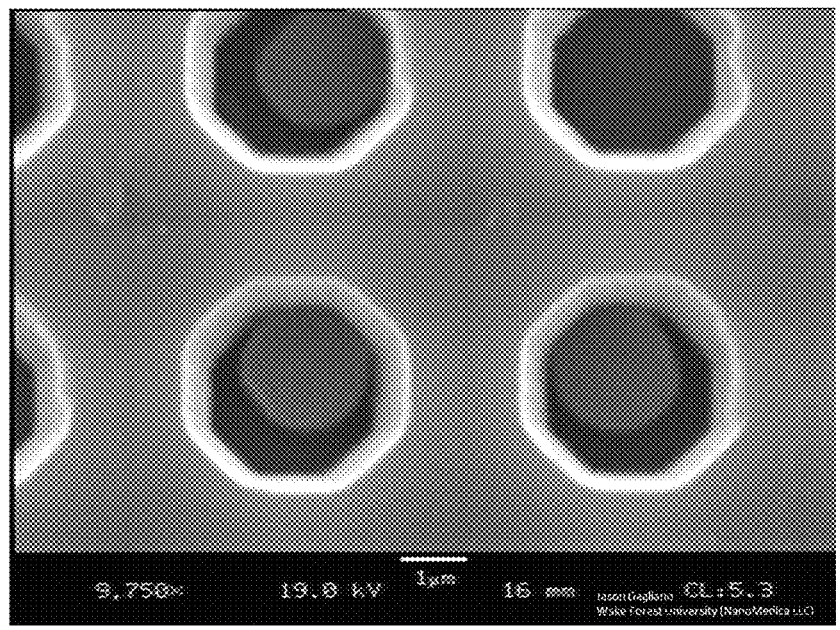

FIG. 7 is an electron micrograph of an ION TORRENT 314 spatially addressable FET array, with beads deposited in some of the wells.

Figure 8:
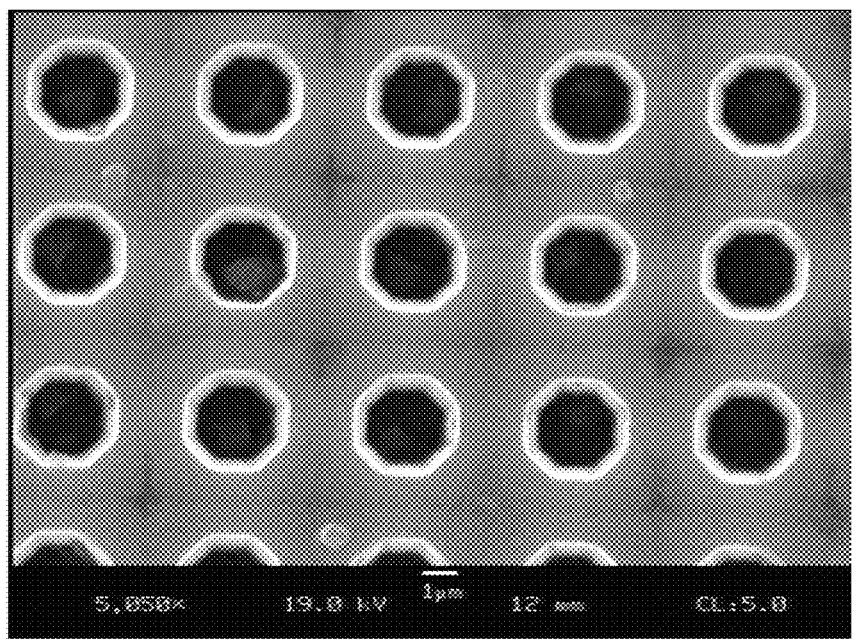

FIG. 8 is an electron micrograph of a portion of an ION TORRENT 316 spatially addressable FET array, with beads deposited in some of the wells.

Figure 9:
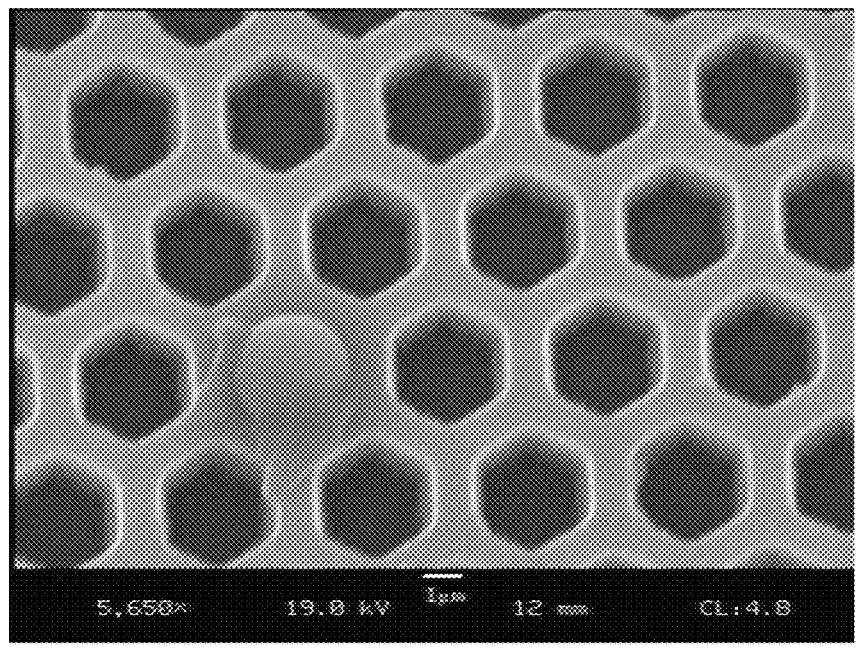
Figure 10:
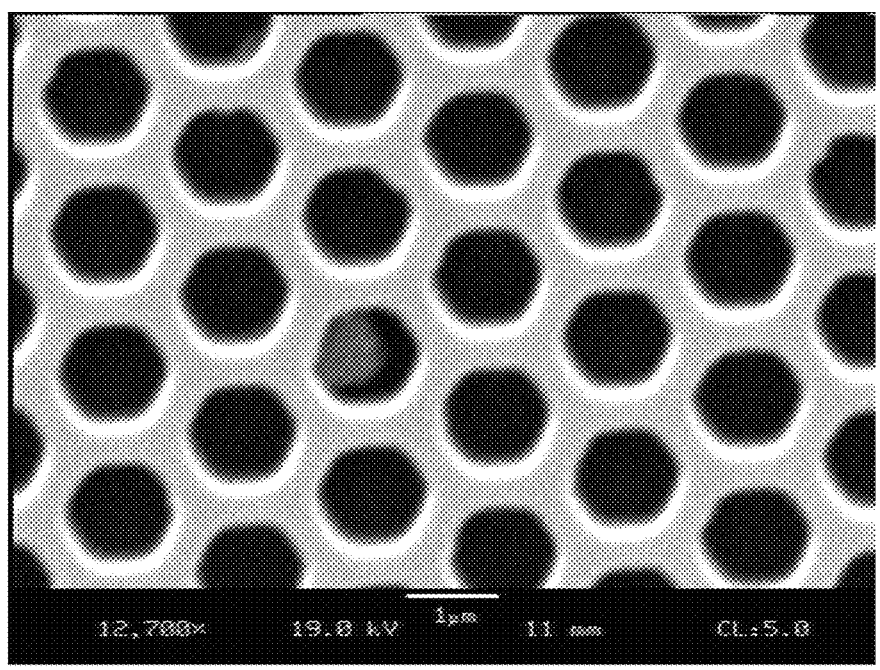
Figure 11:
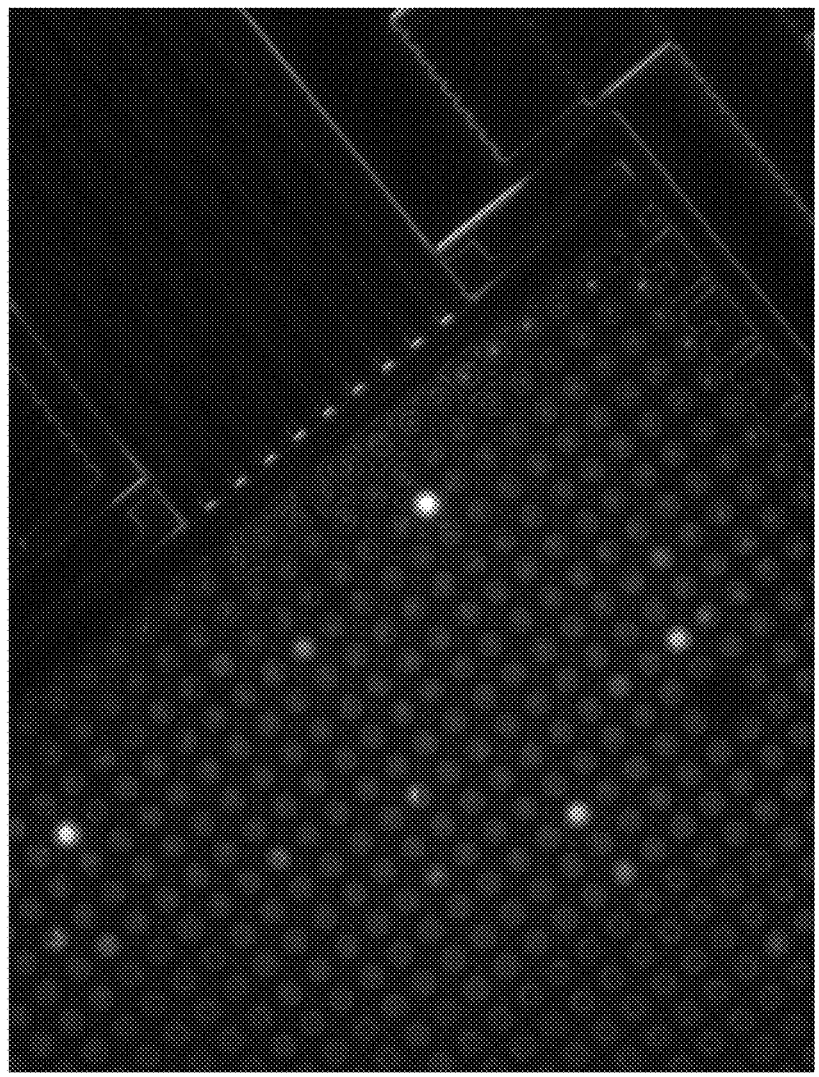

FIG. 9 is an electron micrograph of an ION TORRENT 318 spatially addressable FET array, with beads deposited in some of the wells FIG. 10 is an electron micrograph of an ION PROTON I spatially addressable FET array, with beads deposited in some of the wells FIG. 11 is a fluorescent micrograph image of an ION TORRENT 314 spatially addressable FET array like that shown in FIG. 11 above, with beads having an oligonucleotide coupled thereto deposited in some of the wells, and imaged by fluorescence microscopy.

DETAILED DESCRIPTION OF EMBODIMENTS

1. Overview and Non-Limiting Examples

As noted above, the present invention concerns compositions, methods, devices and apparatus for use in screening and/or selecting a library of nucleic acid molecules and/or nucleic acid tagged or encoded molecules for binding to or interaction with a target molecule or substance. Commercial applications include, for example, selection of ligands and effector molecules with desirable target recognition properties for use in drug discovery, pharmaceuticals, biotechnology, drug delivery, diagnostics, medical devices, cosmetics, environmental analysis, veterinary medicine, forensics, high-throughput molecular discovery and in the identification and validation of novel molecular and chemical genetic probes and modulators of biological pathways as well as intracellular, extracellular and membrane structure and function. Selected ligands and effector molecules may be incorporated into analytical, clinical and industrial formulations, devices and systems to provide optimal application-driven performance and user-friendly benefits in the analysis and implementation of target-binding molecules for medical and industrial applications. A benefit of some embodiments is the design and use of sequencing devices for the selection of new chemical entities with desirable target-binding and/or effector properties for a wide array of applications in clinical medicine, industrial applications and, more generally, analytical, therapeutic, diagnostic and monitoring procedures. A specific example of the clinical and commercial utility of the methods and devices disclosed herein is discovery of therapeutic aptamers, peptides, proteins and low molecular weight synthetic compounds against cell-surface receptors and signaling pathways implicated in oncogenesis, including HER2, overexpressed in breast, prostate and ovarian tumors, and nucleolin, which is elevated in a wide range of cancers.

In some embodiments, the invention comprises:

(1) Sequencing device with a spatially addressable array; this class of devices includes a sequencing device, e.g., a chip, array or flow cell, with spatially addressable locations, optionally populated by nucleotide-modified beads (each bead having multiple copies of a single sequence bound to it) or polonies (regions on a solid substrate that have specific regions with multiple copies of a defined sequence immobilized on, localized to or otherwise operably attached to a spatially addressable location in or on the substrate). The output is the sequence and location of each bead, polony or spatially concentrated region of single sequence per site oligonucleotides or nucleotide-encoded candidate chemicals.

(2) Library of compounds—Compound-containing libraries are exposed to non-sequencing components (distinct from components required for sequencing), such as candidate chemicals, target molecules and analytical reagents for the structural or functional assay and/or characterization of target-binding molecules. In essence, one embodiment of this invention includes introduction of bridge molecules (that connect target-binding candidate chemicals with their associated detection reagents) that therefore connect sequence and location information with information regarding the locations and properties of target-binding molecules. More specifically the library of compounds can be candidate chemicals (e.g., a library of candidate chemicals such as drug candidates and/or analyte-binding diagnostic ligands), that are to be screened against target(s) of interest. Multiple copies of each compound in the library are located at each spatial address in the array.

(3) The target or multiple targets include, e.g., a cancer marker like HER2 or a diagnostic analyte such as thyroxin, testosterone, digoxin or troponin or a panel of targets, e.g., cytokines, involved in a particular signaling pathway). Prospective targets include proteins, enzymes, hormones, disease markers, metabolites, diagnostic analytes and molecules involved in signaling, transmission, biologic function as well as nonbiologic analytes of commercial interest for applications ranging from detection of environmental, veterinary or clinical analytes and precursors and products relevant to industrial production and processing.

(4) Target-binding detection—Detection of target-binding candidate chemicals relies on methods and apparatus to identify candidate chemicals through, e.g., labeling of target molecules (e.g., via fluorescent, colorimetric, enzymatic, luminescent and alternative means for target-specific labeling), so that the binding of a target to a chemical compound can be detected using optical, electromagnetic, physical, electrochemical, luminescent, thermal, mechanical, acoustical, radioactive or other analytical mean. In one embodiment, detection of target-binding does not require labeling of target-binding molecules or optical detection, favoring alternative detection schemes that rely on the intrinsic properties or functions of target-binding molecule, e.g., enzymatic activity, redox activity, absorbance, fluorescence or other native signaling properties.

(4) Quantification of target binding properties of candidate chemicals In some embodiments, a feature of some embodiments over prior art sequencing and molecular discovery technologies is the ability to detect, quantify and characterize the binding of target molecules to sequenceable candidate chemicals in situ on a sequencing device, array or chip. Quantification of target binding includes not only detection of target molecules bound to a particular candidate molecule localized at an addressable sequencing site, well or region, but also determining the amount of target bound, the dissociation kinetics of target binding to different candidate chemicals displayed on a sequencing device, the specificity of candidate molecules for a particular target and the influence of candidate molecule binding on the function or activity of the target molecule. Detection of target molecules bound to candidate chemicals is achieved either by direct labeling target molecules, e.g., using fluorescent, colorimetric or isotopic labeling moieties, by direct detection of the chemical or physical properties of candidate-bound target molecules (e.g., fluorescence in the case of doxorubicin) or through use of labeled secondary affinity reagents such as fluorescently labeled anti-target antibodies, peptides, proteins, coenzymes or affinity probes. In some embodiments, quantification of target binding properties includes assessment of the influence of candidate chemical binding on the structural or functional properties of target molecules. For example, the catalytic activity of enzyme targets (e.g., kinases, phosphatases and dehydrogenases) can be determined in situ on sequencing chips using well-established colorimetric, fluorescent and isotopic enzyme assays. In addition, the specificity of candidate chemical binding to target molecules can be assessed through on-chip competitive assays through which labeled target molecules compete with unlabeled target molecules for binding to candidate chemicals. As specific binding is dose-dependent, saturable and complies with the kinetics of drug-receptor interaction, inhibition curves for labeled target binding in the presence of varying amounts of unlabeled target can be used to determine whether binding is specific, e.g., saturable and dose-dependent, or nonspecific, e.g., refractory to competition by unlabeled target molecules. Another target binding property of candidate chemicals selected by the instant methods is the kinetics of binding and dissociation, which related to the affinity of the candidate molecule for its cognate target. Kinetic parameters of ligand-target interactions disclosed herein are determined in situ on sequencing devices through successive measurements over time of the signal resulting from intrinsic properties, direct labeling or secondary labeling of target molecules. Direct and secondary labeling techniques, reagents, kits and detection schemes, including, e.g., direct fluorescence, absorbance, luminescence and enzyme-driven optical and electrochemical methods, are well known in the art of specific binding assays. In addition to quantification of target binding and target-binding properties of candidate chemicals, methods disclosed herein provide means for assessing structural properties of target-bound or target-binding candidate oligomers, including identification of single-stranded, double-stranded and quadruplex features of candidate oligomers at defined sites in the sequencing array before and after exposure to target molecules. Identification of these structural features is achieved through use of structure-selective probes, dyes and fluorophores specific for secondary structural elements as well known in the art.

In some embodiments, the present invention can be also used to determine in situ and in real-time the dissociation constant between a compound and a target. For example, in one implementation, after binding of the target has been detected, the system is washed to remove free target. Compound-bound target (e.g. target bound to compound on bead) will dissociate over time and diffuse away. Thus, the detected signal (e.g. fluorescence) from the compound-bound target will decay over time. Typically, for simple, bi-molecular dissociation reactions the observed signal will decay as $$I(t)=I_0 \cdot e^{-k \cdot t},$$

where I(t) is the observed signal at some time t; $I_0$ is the signal at the start time $t_0$; and k is the dissociation constant between the target and the compound. In this case, k can be obtain from the negative slope of a plot of ln{I(t)} vs. t.

When it comes to quantification, means for detecting signals from target-bound candidate molecules include, without limitation, an electron microscope, an optical microscope, an absorbance-based microscope, a photon detection system, an acoustic detection system, a surface plasmon resonance detection system, a thermal detection system, an electromagnetic detection system, a waveguide, a CCD camera, a confocal microscope, a laser-scanning device, a fluidic and/or mechanical detection system and an isotopic detection system and elemental analysis, including, e.g., x-ray scattering.

2. Definitions

"Sequenceable molecule" as used herein refers to a chemical compound or composition for which the primary sequence, encoding sequence or identifying sequence segment can be determined. Among the biopolymers that are sequenceable are nucleic acids such as RNA, DNA, modified RNA, DNA, PNA; proteins, peptides and synthetic heteropolymers comprising naturally occurring and non-naturally occurring nucleotide bases, amino acids, backbones and intermonomer linkages, as are well known in the art. Advantageously, methods and devices of some embodiments of the present invention can be used to select target-binding ligands that are not directly sequenceable themselves. For example, PNA bases are not recognized by nucleotide-binding enzymes traditionally used for nucleic acid amplification and/or sequencing. Similarly, although encoded small molecules are not themselves directly sequenceable, use of tag sequences and encoding strategies described herein renders them identifiable by sequencing of tag and/or encoding sequences.

"Tag sequence" as used herein refers to a unique sequence of monomers which is attached to a candidate chemical, is complementary to a part of a sequenceable molecule, and which serves to hybridize to a sequenceable molecule. In some embodiments the tag sequence is a nucleic acid having, from 5' to 3', the general formula A-B-C, where A is an optional primer segment, B is a variable segment, and C is an optional primer segment. Primer segments A and C are, in general, from 8 or 10 nucleic acids in length up to 100 or 200 nucleic acids in length, or more. Variable segment B is, in general, from 10 or 20 nucleic acids in length up to 1000 nucleic acids in length, or more. While each variable segment is unique for the corresponding connected candidate chemical, primer segments are preferably the same for all connected different candidate chemicals, so that each unique identifier can be amplified by the same amplification reaction. Inactive segments may be included if desired. In some embodiments A and C are both present and are corresponding forward and reverse primer segments; in some embodiments one or the other of A and B is omitted and only a single primer segment is included.

"Candidate chemical" as used herein refers to a chemical compound, optionally a polymer, heteropolymer or conjugate of two or more molecules, which is used in the context of a "test compound" or a "drug candidate compound" used in connection with the screening and selection assays described herein, advantageously the screening and selection of new chemical entities with target-binding and/or target-modulating properties. Such chemicals comprise organic or inorganic compounds, including monomers, polymers, heteropolymers and complexes or conjugates thereof, which are derived synthetically or from natural sources. Candidate chemicals are, in some embodiments, preferably small molecules. In other embodiments, they are preferably higher molecular weight compounds, including various macromolecules, biomimetic polymers and synthetic polymers well-known in the art, e.g., nucleic acids, peptides, nucleopeptide conjugates, glyoconjugates, chimera, hybrid molecules and the like.

"New chemical entity" as used herein means a previously undiscovered nongenomic sequence or sequence-encoded nonnucleic acid molecule with desirable target-binding and/or target-modulating properties.

"Detectable" as used herein refers to a target molecule, e.g., protein, peptide, small molecule, therapeutic target or diagnostic analyte that can be detected on a sequencing chip via optical (e.g., fluorescent or colorimetric), electrical, magnetic, thermal, chemical, mechanical, electrochemical, fluidic, isotopic, radioactive, or other signaling means known in the art.

"Directly-sequenceable" as used herein refers to a chemical compound or composition attached to or incorporated within a sequenceable molecule for which the primary sequence or an identifying sequence segment thereof can be determined by sequencing, preferably next-generation sequencing, on-chip sequencing and/or sequencing without prior amplification.

"Operably connected" as used herein refers to an attachment of one molecule to another in such a configuration that the relevant function(s) of each molecule operably connected is/are not destroyed during screening, selection and sequencing processes described herein. For example, a sequenceable molecule operably connected to a microscopic bead must retain its ability to hybridize to its complementary tag molecule. Similarly, for a tag molecule operably connected to a candidate chemical, the tag molecule must retain its ability to hybridize to its complementary sequenceable molecule, while the candidate chemical must retain its ability to bind to and/or functionally interact with its target molecule. In a preferred embodiment, "operably connected" refers to a covalent linkage. However, non-covalent linkages, such as chelation, antigen-antibody complexes, and other types of bonding may also be utilized.

A nucleic acid (NA) sequenceable molecule may be attached to a microscopic bead in any manner known in the art. Numerous methods exist in the art for attaching the NA molecules to solid supports such as microscopic beads. In one aspect, covalent chemical attachment of the NA to the bead can be accomplished by using standard coupling agents, such as water-soluble carbodiimide, to link the 5'-phosphate on the NA to amine-coated capture beads through a phosphoamidate bond.

Another alternative is to first couple specific oligomeric linkers, e.g., oligonucleotides, to the bead using similar chemistry, and to then use an appropriate enzyme or catalyst (e.g., ligase) to link the NA to the linker on the bead. Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially.

Other linkage chemistries to join an oligonucleotide to a bead include the use of N-hydroxysuccinamide (NHS) and its derivatives. Homopolymer linkers may also find utility in certain applications. By employing oligo-dT coupled to the bead, it is possible to hybridize to the poly-A tail found in mRNA as a means for directly sequencing mRNA isolated from cells.

Yet another method for coupling NA to beads employs specific ligands attached to the end of the NA to link to ligand-binding molecules attached to the bead. For example, a terminal transferase can be used to incorporate such a ligand onto the end of the DNA, oligonucleotide linkers already containing an appropriate ligand can be ligated to the DNA, or oligonucleotides capable of forming a stable triple-helix with a target duplex DNA can be synthesized to incorporate an appropriate ligand (see, e.g., Smith et al., "Direct Mechanical Measurements of the Elasticity of Single DNA Molecules by Using Magnetic Beads," Science 258:1122-1126, 1992, which is incorporated herein by reference).

In one particular embodiment in which the DNA contains the appropriate single-stranded telomeric recognition site, telomere terminal transferase (Greider et al., 1987, Cell 51:887-898, which is incorporated herein by reference) can be used to incorporate a biotinylated nucleotide at the 3' end of the DNA which can then be bound to a secondary capture reagent such as avidin, streptavidin or related biotin-binding molecules immobilized on the bead. In this embodiment, a 5' to 3' exonuclease can then be used for sequencing, since the 3' end is the "tethered" end. Other secondary capture reagents such as hapten-binding antibodies are well known in the art In yet another embodiment, calf thymus terminal transferase (Kato et al., 1967, J. Biol. Chem. 242:2780, which is incorporated herein by reference) can be used to incorporate a ligand-linked nucleotide onto the 3' end of any DNA molecule with a free 3' hydroxyl group. U.S. Pat. No. 6,420,112 also describes a method for attaching nucleic acids, such as DNA, to microscopic beads or other support structures using a terminal transferase.

In still another approach, a DNA-binding protein can be coupled to the bead by chemistries well known in the art and in such a fashion that the DNA-binding site is unperturbed. DNA containing the recognition sequence for the DNA-binding protein can thereby be coupled to the bead.

"Ligand-binding partner pair" as used herein refers to a pair of molecules which exhibit strong affinity and specificity.

"Ligand" means any substance capable of specifically binding to a target. Ligands include but are not limited to, agonists, antagonists, carbohydrates, lipids, drugs, hormones, transmitters, cofactors, vitamins, toxins, oligonucleotides, nucleic acids, aptamers, and conjugates formed by attaching any of these molecules to a second molecule. Ligand-binding partner pairs are pairs of molecules that exhibit mutual affinity and specificity. Such pairs include, but are not limited to, ligand-target complexes, biotin-avidin/streptavidin/neutravidin, or various antibody/antigen pairs such as digoxygenin-anti digoxygenin.

"Unique identifier" as used herein refers to any identifier which is guaranteed to be unique among all identifiers used for a given set of objects and specific purpose. In particular, for a sequenceable molecule, its complementary tag molecule, and the candidate chemical operably connected to the tag molecule, there is a unique and unambiguous relationship between the molecules in that group.

"PNA" as used herein refers to Peptide nucleic acid. PNA is an artificially synthesized polymer similar to DNA or RNA. PNA is not known to occur naturally. The PNA backbone is composed of repeating N-(2-aminoethyl)-glycine units linked by peptide bonds, unlike DNA and RNA, which, respectively, have a deoxyribose and ribose sugar backbones. Purine and pyrimidine bases are linked to the PNA backbone by methylene carbonyl bonds. PNA is an effective structural mimic of DNA and RNA, and PNA oligomers are able to form very stable duplex structures with Watson-Crick complementary DNA, RNA, or PNA oligomers.

"Modified DNA" as used herein refers to a DNA molecule which has been chemically modified, while retaining the ability to form very stable duplex structures by Watson-Crick complementary with other DNA, modified DNA, RNA, or PNA oligomers. Examples of modified DNA include molecules modified at the base moiety, sugar moiety or phosphate backbone to improve, e.g., the stability and/or hybridization properties of the molecule.

For example, the deoxyribose phosphate backbone of the nucleic acid molecules can be modified to generate peptide nucleic acids, glycerol nucleic acids, locked nucleic acids, threose nucleic acid, and phosphorodiamidate morpholino oligos.

Examples of modified nucleotides which can be used to generate a modified nucleic acid include base-boronated dinucleotides, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

"Polymerase chain reaction" or "PCR" as used herein refers broadly to a process for amplifying DNA by in vitro enzymatic replication using a DNA polymerase, usually a heat-stable DNA polymerase such as Taq polymerase; deoxynucleoside triphosphates (dNTPs); and oligonucleotide primers. The DNA generated in each PCR cycle is used as a template in the next cycle, and the DNA template is exponentially amplified.

There are many variants of PCR well known in the art. One of the most common is "reverse-transcriptase polymerase chain reaction" or "RT-PCR", a common method used to amplify RNA. In RT-PCR, use of reverse transcriptase, an enzyme that converts RNA into cDNA, precedes PCR. Among the PCR variants, the following are most relevant to the disclosed subject matter:

Multiplex-PCR can involve up to a dozen pairs of primers acting independently. This modification is used to simultaneously analyze multiple targets in a sample.

Isothermal amplification is an approach to amplify nucleic acid that uses only single temperature incubation, whereas regular PCR uses three different temperatures for primer annealing, primer extension and denaturation.

Asymmetric PCR is used to preferentially amplify one strand of the target DNA, and is used where having only one of the two complementary strands of the product is advantageous. PCR is carried out as usual, but with a limiting amount of one of the primers. When it becomes depleted, continued replication leads to an arithmetic increase in extension of the other primer and its corresponding DNA. A recent modification on this process is known as Linear-After-The-Exponential-PCR (or LATE-PCR).

Hot-start/cold-finish PCR is achieved with hybrid polymerases that are inactive at ambient temperature and are only activated at elevated temperatures. In Touchdown PCR, the temperature used to anneal the primers is gradually decreased in later cycles. The initial higher annealing temperature, 3-5° C. above the standard melting temperature of the primers used, leads to greater specificity for primer binding, while lower temperatures permit more efficient amplification at the end of the reaction.

All of the PCR variants enumerated herein, and others not explicitly identified, are understood to involve routine optimization of the basic PCR process, and are intended to be within the broad scope of the term "PCR" as used herein. So long as a particular technique serves the purpose of amplifying DNA by in vitro enzymatic replication using a DNA polymerase, deoxynucleoside triphosphates, and oligonucleotide primers, it is considered within the scope of the present claims.

"Library of candidate molecules" and "candidate library" refer to populations of molecules to be screened and/or selected for target-binding and/or functional properties. Candidate molecules may be sequenceable molecules, nucleic acid molecules, nucleotide-encoded molecules, biopolymers, synthetic heteropolymers, nucleotide-tagged chemicals and the like.

"Library of tagged chemicals" as used herein refers to a plurality of candidate chemicals, the corresponding tag sequence of each candidate chemical, and the sequenceable molecule complementary to each tag sequence. In some cases, e.g. aptamers, the tag is also the chemical. In this case, it might be more appropriate to call them simply a 'Library of compounds'.

"Target molecule" and "target" as used herein refer to a molecule which is the target for testing for a desired interaction with one or more candidate chemical(s). A target can be any substance capable of specifically binding to or interacting with a ligand. Target molecules include, for example, small molecules, antibodies, antibody fragments, antibody mimetics, molecular mimics and molecular imprints, molecular recognition units, adhesion molecules, soluble receptors, avidin, streptavidin, lectins, selectins, oligonucleotides, nucleic acids, membrane receptors, cellular receptors, drug receptors, proteins, peptides, fusion molecules, recombinant molecules, viruses, bacteria, membrane preparations, lipids, carbohydrates and conjugates, hybrids or complexes thereof.

"Specific binding" refers to the saturable, affinity-based interaction between a ligand and a target which is well known in the art.

"Hybridization" refers to specific binding between two or more nucleic acid sequences through complementary base pairing. Such binding is also referred to as Watson-Crick base pairing. For hybridization, a sufficient degree of complementarity is required to yield reversible binding between two selected nucleic acid sequences. Perfect complementarity is not required and may not be preferred for embodiments relying on reversibility, such as dissociation of a hybridized nucleic acid sequences.

"Stringent" as used here refers to hybridization conditions that are commonly understood in the art to define the commodities of the hybridization procedure. Stringency conditions can be low, high or medium, as those terms are commonly known in the art and well recognized by one of ordinary skill. High stringency hybridization conditions that will permit homologous nucleotide sequences to hybridize to a nucleotide sequence as given herein are well known in the art. As one example, hybridization of such sequences to the nucleic acid molecules disclosed herein can be carried out in 25% formamide, 5×SSC, 5×Denhardt's solution and 5% dextran sulfate at 42 degrees C., with wash conditions of 25% formamide, 5×SSC and 0.1% SDS at 42 degrees C., to allow hybridization of sequences of about 60% homology. Another example includes hybridization conditions of 6×SSC, 0.1% SDS at about 45 degrees C., followed by wash conditions of 0.2×SSC, 0.1% SDS at 50-65 degrees C., at, for example, about 60, 70, 80 or 90 percent homology, or more. Another example of stringent conditions is represented by a wash stringency of 0.3 M NaCl, 0.03M sodium citrate, 0.1% SDS at 60-70 degrees C. using a standard hybridization assay (see SAMBROOK et al., EDS., MOLECULAR CLONING: A LABORATORY MANUAL 2d ed. (Cold Spring Harbor, N.Y. 1989, the entire contents of which are incorporated by reference herein). In various embodiments, stringent conditions can include, for example, highly stringent (i.e., high stringency) conditions (e.g., hybridization to filter-bound DNA in 0.5 M $NaHPO_4$, 7% sodium dodecyl sulfate (SDS), 1 mM EDTA at 65 degrees C., and washing in 0.1×SSC/0.1% SDS at 68 degrees C.), and/or moderately stringent (i.e., medium stringency) conditions (e.g., washing in 0.2×SSC/0.1% SDS at 42 degrees C. See, e.g., U.S. Pat. No. 7,645,602).

"Highly stringent conditions" as used herein refers to the conditions under which a sequenceable molecule will hybridize to its tag sequence, to the exclusion of other sequences. This is also known in the art as homologous probing. Highly stringent conditions are sequence-dependent and will be different in different circumstances. By controlling the stringency of the hybridization and/or washing conditions, a tag sequences and its corresponding candidate chemical can be identified which is 100% complementary to the sequenceable molecule. Generally, highly stringent conditions are selected to be less than about 5° C. lower than the thermal melting point for the specific sequence and its complement at a defined ionic strength, wash conditions, pH, and percentage of destabilizing agent(s) such as formamide. Stringency conditions are known in the art and can be found, for example, in Current Protocols in Molecular Biology (John Wiley & Sons, New York (1989), 6.3.1-6.3.6 which is incorporated herein by reference). Further, an extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Inter science, New York (1995), which are incorporated herein by reference.

"Nucleic acid molecule" refers to biological, naturally occurring, nonbiological and synthetic nucleotides, oligonucleotides and nucleic acid sequences which may optionally be conjugated to one or more nonoligonucleotide molecules.

"Nucleotide" includes nucleotides and nucleotide analogs, preferably groups of nucleotides comprising oligonucleotides, and refers to any compound containing a heterocyclic compound bound to a phosphorylated sugar by an N-glycosyl link or any monomer capable of complementary base pairing or any polymer capable of hybridizing to an oligonucleotide, including nucleotide-containing polymers having modified backbones or nonnaturally occurring bases.

"Nonnucleic acid molecule" means a molecule or group of molecules that is not a nucleic acid.

"Effector" and "effector molecule" as used herein refer to a selected candidate molecule, e.g., a ligand, whose interaction with a target molecule affects or modulates the structure and/or function of the target molecule.

"Sequential sequencing" as used herein refers to repeated use of a spatially addressable sequencing array to sequence candidate chemicals before and after target binding and/or to perform a series of sequencing reactions at different stages of target binding, functional and/or structural analysis.

"Parallel sequencing" as used herein refers to the use of two or more sequencing devices (e.g., spatially addressable sequencing arrays) to determine the sequences of sequenceable molecules under different conditions, e.g., a first sequencing device to determine sequences of a library of sequenceable molecules and a second sequencing device used to determine sequences of the library of sequenceable molecules following exposure to one or more target molecules, optionally including a fixation step to covalently attach noncovalently bound target molecules to their cognitive sequences or sequence encoded candidate chemicals.

"Cognate sequence" and "cognate target," as used herein, refer to candidate molecules and/or corresponding target molecules that specifically bind to or interact with one another.

3. Target Molecules

Any suitable target molecule can be used in carrying out the present invention, including but not limited to proteins, peptides, and nucleic acids. In some embodiments, the target molecules are enzymes (such as kinases), receptors (such as G-protein coupled receptors), and ion channels (such as voltage-gated sodium channels). In some embodiments, target molecules are unlabeled, which is to say that they have not been covalently modified prior to exposure to candidate chemicals. In this way, the target-binding effector activities of candidate chemicals accurately reflect candidate interaction with native, unmodified targets.

4. Spatially-Addressable Arrays

Spatially addressable arrays for high-throughput sequencing, also known as Next-Generation Sequencing (NGS) arrays, are known and numerous alternative designs are available. NGS arrays include, e.g., sequencing systems available through Life Technologies and their subsidiaries and competitors, including Pacific Biosciences, Illumina, 454 Sequencing and the like. In general, such arrays comprise a surface portion having a plurality of separate and discrete locations formed thereon, with a different oligomer immobilized at each of said separate and discrete locations. The identity of the oligomer at each location is known (by any suitable technique—typically determined through controlled synthesis, deposition or attachment of a specific oligomer, or the coupling of a particular monomer within that oligomer, at one or more locations). Spatially addressable arrays may be one-dimensional (or "linear" arrays) or multidimensional. In some embodiments, two dimensional arrays, or three-dimensional arrays are preferred. Any suitable technique may be used to determine binding or hybridization of a molecule to an oligomer at each of the separate and discrete locations, including optical, magnetic, mechanical, chemical, nuclear (radioactive and/or isotopic), and electrical techniques.

In some embodiments, the spatially addressable array is an optical (e.g., a "CD" or "CD-ROM") array. See, e.g., U.S. Pat. No. 7,094,609.

In some embodiments, the spatially addressable array is a field-effect transistor (FET) array. See, e.g., U.S. Pat. No. 7,948,015 (Life Technologies); see also J. Rothberg et al., *Nature* 475, 348-352 (Jul. 21, 2011) (Ion Torrent by Life Technologies). In other embodiments, the spatially addressable array is an array of polonies. See, e.g., HiSeq™ Sequencing System and MiSeq™ Personal Sequencer (Illumina, Inc. San Diego, Calif.).

Spatially addressable arrays of some embodiments of the invention can be used to determine nucleotide sequences of oligomers disposed at defined locations within the spatially addressable array. Thus, spatially addressable arrays are advantageously "spatially addressable sequencing arrays," also referred to as "sequencing arrays."

5. Candidate Chemicals

As noted above, any suitable library of candidate chemicals can be used in the present invention, and from which the candidate molecule can be selected. In some embodiments, the candidate chemicals are small molecules, in other embodiments they are members of randomer or combinatorial sequence or shape libraries comprising sequenceable oligomers from which target-binding aptamers are selected, including aptamers with modified backbones, sugars or bases. In other embodiments, the candidate chemicals are conjugates, chimera or modular constructs with nucleotide and nonnucleotide regions.

"Small molecule" as used herein is defined as a molecule with a molecular weight that is less than 10 kD, typically less than 2 kD, and preferably less than 1 kD. Small molecules typically have a molecular weight of 100, 200, or 300 Daltons or more. Small molecules include, but are not limited to, inorganic molecules, organic molecules (e.g., peptides, glycopeptides, amido peptides, etc.) organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Oft et al., US Pat. Appln. Publication No. 20100003251 (Jan. 7, 2010); see also U.S. Pat. No. 6,326,482). An extensive list of example compounds that may be small molecules or candidate chemicals used in the embodiments described herein is set forth in W. Hunter, et al., US Patent Application Publication No. 20050181977 (Published Aug. 18, 2005) (see paragraphs 0065 through 0387 therein), the disclosure of which is incorporated by reference herein in its entirety.

In some embodiments, the candidate chemicals are synthetic small molecules. In one embodiment, they are macrocyclic compounds, which macrocyclic compounds are produced or synthesized on their corresponding tag sequence by template-directed synthesis using the tag sequence as a template. See, e.g., R Kleiner et al., *J Am.*

Chem. Soc. 132, 11779-11791 (2010). In some embodiments, candidate chemicals are nucleic acids or encoded monomers, peptides, polymers, macromolecules or conjugates or hybrids thereof.

6. Methods and Apparatus

In a brief overview, FIG. 1 schematically depicts the four steps of one non-limiting embodiment of the invention, as follows:

Step 1) Ion Torrent Sequencing (ITS). Complementary sequences of each macrocycle's coding DNA are attached to micron-size beads using emulsion PCR (em-PCR) and sequenced with the Ion Torrent Personal Genome Machine (PGM) in accordance with known techniques. In ITS, each bead is sequenced individually in a micrometer-sized well. There are millions of wells per sequencing chip. The DNA coding sequence for each macrocycle is about 100 bp long, an ideal length for this approach. The outcome of ITS is an array file that lists the sequence and well locations (address) for each bead; i.e., the sequence and position of each bead are known. In addition, the chip can be used for decoding and analyzing library drug candidates, as outlined in steps 2-4 below. Step 2) Macrocycle hybridization. A macrocycle library (of macrocyclic compounds conjugated to nucleic acid tags, or bar codes) is hybridized to the beads in the wells of the Ion Torrent PGM. Beads are firmly lodged, but accessible in the wells. Step 3) Target binding. Target molecules are flowed across the chip containing the beads with attached macrocycles, and any binding will result in a strong signal, which can be optical (detect photons as in brightfield, DIC, or fluorescence microscopy) or a current, provided that target binding or catalytic activity releases ions, which the Ion Torrent PGM can detect. Step 4) Dissociation constant. After a wash step, the lifetime of the signal, a measure of the affinity for each binding pair, is determined in situ (on chip).

7. Structural and/or Functional Analysis of Target-Binding Molecules

The structural and/or functional properties of target-binding molecules can be determined in situ on sequencing devices or through in vitro or in vivo assays following removal from a sequencing device. Target-binding molecules can be removed from the sequencing device either by elution of beads (or other substrates) containing immobilized molecules or by isolation of individual species (e.g., single beads or members of single polonies) Alternatively, candidate molecules can be first dissociated from beads or other surfaces and then removed and analyzed in vitro or in vivo.

Determination of binding properties (e.g., dissociation kinetics, target-binding specificity, affinity estimates) and high-content characterization of ligand-target interactions can be achieved through use of accessory reagents such as structure probing molecules and signal generating species, including, e.g., natural, fluorogenic, colorimetric of luminescent enzyme substrates, cofactors or coenzymes.

Structure probing reagents and methods for RNA and DNA analysis are well known in the art. In one embodiment, structure probing of candidate nucleic acid molecules is performed in situ on sequencing devices followed by in situ resequencing. In another embodiment, structure probing is performed offline following sequencing following either in situ or offline addition of structure probing reagents.

"Signal-generating species" refers to molecules or groups of molecules capable of generating a detectable signal or enhancing or modulating the detectability of a substance or transducing an energy, activity, output or signal of a substance into a qualitatively, quantitatively or detectably different energy, activity, output, signal, state or form. Signal-generating species include, but are not limited to, molecules, groups of molecules, conjugates and complexes comprising detectable (and optionally dyed, modified, conjugated, labeled or derivatized) tags, tracers, radioisotopes, labels, reporters, polymers, natural and synthetic and biomimetic photosynthetic molecules, reaction centers, photosystems, signal transduction pathways, molecular cascades, macromolecules, microparticles, nanoparticles, colloids, metals, dyes, fluorophores, phosphors and other photon-absorbing, photon-emitting and photosensitive molecules, molecules or groups of molecules that enhance, attenuate, modulate or quench the photon-absorbing or photon-emitting properties of another molecule or group, energy transfer donors and acceptors, enzymes, coenzymes, cofactors, catalytic antibodies, synthetic enzymes and catalysts, molecular mimics and mimetics, luminescent, triboluminescent, sonoluminescent, electroluminescent, chemiluminescent and bioluminescent molecules, electron transfer donors and acceptors, oxidizing and reducing compounds, mediators and other electroactive molecules, metabolic, photoactive, signaling and signal-processing molecules used to capture and transduce energy or information in biological and biomimetic processes and systems. Signal generation species may be added to sequencing devices followed by direct in situ signal detection or in any combination of in situ or offline addition and detection.

8. Additional Aspects of Some Embodiments

Cost Benefits:

Another aspect of some embodiments is the ability to reduce the cost and time required for molecular discovery by orders of magnitude relative to existing alternative methods, devices and systems. Cost savings are achieved not only by time and labor reduction, but also dramatic decreases in sequencing reagent costs. In NGS roughly the same quantity of reagents are used to obtain >1,000,000 sequences as were used in historic methods (e.g., Sanger sequencing) to determine a single sequence. Thus, even if we anticipate only a few hundred hits per target, the present integrated compound discovery systems and methods will reduce costs a thousand- to million-fold. Further, the cost of selection reagents (candidate libraries and target molecules) is correspondingly decreased, allowing screening and selection of libraries containing millions to billions (or more) of candidate members using femtomoles or less amounts of target molecule and, conservatively, <100 femtomoles of, e.g., a million-member library.

Sequential and Multiple Use Devices.

Another feature of some embodiments is transformation of next-generation sequencing chips from unit-use disposable devices to sequential-use devices capable of providing information on the structural and/or functional properties of sequences determined by instrumented analysis. We have demonstrated that certain types of sequencing chips, e.g., those relying on bead-immobilized nucleic acids, can be washed, dried and stored for subsequent analysis. Sequential on chip analysis of single-sequence-per-site functional properties (such as target-binding, enzymatic and/or regulatory activities) or structural properties (secondary or tertiary structures or conformational transitions) can provide high-content information on candidate chemicals and their interactions with target molecules without the high cost, time and labor required to perform such analyses through multiple runs using multiple chips. This feature of some embodiments includes provision of reagents, kits and accessories to NGS sequencing laboratories that enable high-content sequencing and selection of candidate nucleic acids or nucleotide-encoded molecules for desired structural or functional properties through repeated sequencing and/or detection steps on a single chip.

Another feature(s) of some embodiments is the ability to perform on-chip structural or functional selection in either "forward selection," "reverse selection" or "dual selection" modalities. "Forward selection" means that libraries are first exposed to target substances, which may be structural or functional probes, followed by separation/selection of candidate molecules with desirable properties, next-gen sequencing of selected molecules to identify the selected candidate molecules and on-chip analysis to further select or confirm structural or functional properties in situ. "Reverse selection" means that candidate molecules are selected for structural or functional properties after sequencing reactions are performed (albeit not necessarily before sequencing data has been reduced to sequence information) and then followed by on-chip determination of structural or functional properties of selected nucleic acids or nucleotide-encoded molecules.

Another feature of some embodiments is to transform previously processed, heretofore disposable sequencing chips into higher value molecular selection devices, which transformation is enabled by reagent means to determine structural and functional properties of sequenced nucleic acids either in situ on the sequencing chip and/or through single-bead analysis following isolation of individual beads from the sequencing chip.

Embodiments of the present invention can be implemented in a variety of ways. For example, and as schematically illustrated in FIG. 2, the tagged compounds (beads plus attached nucleic acid) can be left as an aptamer library, and the same, or a different, target can be screened for binding to the aptamers. FIG. 3 illustrates a still further example, where multiple targets are used, or the targets are themselves a "lab on bead" constructs as described in Guthold and Macosko, PCT Application WO 2010/091144 (Published Aug. 12, 2010).

The foregoing and other objects and aspects of embodiments of the invention are explained in greater detail in the Examples below.

Example 1

Ion Torrent Sequencing

The first step in ITS is binding copies of each complementary DNA strand in the library to beads by em-PCR. Currently micron-size beads are used in the Ion Torrent PGM, but smaller diameter beads are used in the Ion Torrent Proton. This process is semi-automated in a machine called the OneTouch™ device. Briefly, $8 \times 10^7$ molecules of template DNA, and $3 \times 10^7$ beads are added to 150 ul aqueous PCR solution; this solution is emulsified with 600 ul of oil, resulting in $2 \times 10^9$ aqueous PCR compartments. This emulsion is PCR-amplified for 30 cycles. The outcome of em-PCR, followed by enrichment with the OneTouch ES is a library of unique beads each containing about $10^5$-$10^6$ copies of a specific coding sequence (FIG. 1, step 1A). The beads are then placed on a special chip with 1.3 million wells (314 chip, FIG. 4A), 6.3 million wells (316 chip), or 11 million wells (318 chip). The chip consists of an array of wells with ISFETs (ion sensitive field-effect transistors) that can detect the production of $H^+$ ions when bases are added to oligonucleotide polymers. By flowing nucleotides one at a time over the whole chip, it can read which wells produce a current when the polymerase extending the DNA adds a nucleotide to the single strand on each bead (FIG. 1, step 1B). The data is output to a file, which contains the position (well address) and sequence of each bead. The data can be displayed pictorially (FIG. 4B). This image shows the entire chip, with superimposed sequence read scores for each of the 1.3 million wells. The football shaped map shows whether the well contains a bead with template: white represents an acceptable read, black, a rejected read (too short, indecipherable).

FIG. 4C shows a zoomed brightfield image of the chip after our sequencing run; dark circles with a smaller bright central region indicate a well filled with a bead; solid bright disks indicate empty wells.

In addition, after sequencing, we flowed 2.8-um autofluorescent, magnetic beads over the chip and viewed the chip using fluorescence microscopy (Nikon E600FN with Tucsen cooled camera; FIG. 4D). The wells with magnetic beads (fluorescent) are clearly distinct from those without, which contain Ion Torrent beads with our library DNA.

An analysis of the Fastq data file showed the sequences contained in the compound library. As shown in FIG. 5 these sequences consist of adaptors (primers) on either end, and four codons, A, B, C, and D, which code for groups S, $R_1$, $R_2$, $R_3$. There are twelve unique codons for A, B, C and eight for D, resulting in a library of $12 \times 12 \times 12 \times 8 = 13,824$ members. Larger libraries can be constructed with more codons.

These preliminary experiments included a complete run through all steps of the ITS, including em-PCR to attach the sequence templates of our library to the Ion Torrent beads, an enrichment step, and the final run in the PGM. Additionally, we were able to visualize single beads in their wells via brightfield microscopy (FIG. 4C) and fluorescence microscopy (FIG. 4D).

Example 2

Hybridization of DNA-Encoded Macrocycles

After reading and recording the sequences on the beads in each well, we denature the double-stranded DNA using 0.1 M NaOH (Gassman, N. R., J. P. Nelli, S. Dutta, A. Kuhn, K. Bonin, Z. Pianowski, N. Winssinger, M. Guthold, and J. C. Macosko, 2010. Selection of bead-displayed, PNA-encoded chemicals. Journal of Molecular Recognition 23:414-422). Hybridization is carried out in 40% formamide at 50° C., followed by a wash resuspension in pH 8.8 buffer containing 10 mM Tris, 50 mM KCl, 0.01% Triton X-100, 3 mM $MgCl_2$, and 8% glycerol. We then flow the 50 ul of the library with encoded macrocycles into the chamber to bind to their complementary strands on beads in the wells.

For specific library 1, we use a defined oligonucleotide library that contains a known ratio of a 5'-FITC labeled oligo of known sequence. We test ratios of 1:100, 1:1,000 and 1:10,000. Using em-PCR, bead libraries with complementary strands are created and sequenced. The library containing the FITC oligos is hybridized to the beads in the wells, starting from the conditions noted above. We expect 1/100, 1/1,000, and 1/10,000 of the beads to fluoresce (FITC emits in the green). We then adjust the hybridization conditions until chips yield corresponding 1/100, 1/000 and 1/1000 fluorescent wells. In the target-binding step (step 3, below), a TAMRA-labeled (red fluorescence) anti-FITC antibody is flowed over the beads in the wells.

For specific library 2, we use a library containing 13,824 unique macrocycles, each tagged with a unique, known DNA coding sequence (FIG. 5). We use em-PCR to attach the complementary strands to micron-size beads for ITS. We already successfully sequenced this library in a test run. Using optimal conditions defined in specific library 1, we hybridize the encoded macrocycle library to beads in the wells. In the target-binding step (step 3, below), TAMRA-labeled (red fluorescence) Src kinase is flowed over the beads in the wells.

Example 3

Target Binding

The target (anti-FITC antibody, specific library 1; Src kinase, specific library 2) is labeled with TAMRA (red emission) using a fluorescent kit as we previously reported (Liu, W., C. R. Carlisle, E. A. Sparks, and M. Guthold. 2010. The mechanical properties of single fibrin fibers. J. Thromb. Haemost. 8:1030-1036; Liu, W., L. M. Jawerth, E. A. Sparks, M. R. Falvo, R. R. Hantgan, R. Superfine, S. T. Lord, and M. Guthold. 2006. Fibrin Fibers Have Extraordinary Extensibility and Elasticity. Science 313:634) and introduced to the macrocycles on the beads. After flowing the targets through the chip assembly, we remove the chip and inspect it under a microscope for fluorescence. Specifically, the chip is imaged via epifluorescence with a metallurgic microscope (FIG. 4D). The field of view with a 20×-wide lens is 1 mm$^2$, so we collect 100 raster images of ~1 cm$^2$, which will take about 100 seconds. The beads attached to targets fluoresce brightly red, and since we know the sequence and position of each bead from step 1, we know the identity of each binder. Moreover, as outlined in step 4, we can zoom in to determine the dissociation constant for each macrocycle/target pair.

There is a possibility that an antibody target or protein target will produce a current signal above the level of detection of the Ion Torrent ISFET circuits. If so, fluorescently labeling the target can be eliminated, and the target-binding step can be performed in the Ion Torrent machine instead of a fluorescent microscope. If not, fluorescent labeling or labeled antibodies can be used for virtually all targets of interest.

Example 4

Target Dissociation

The composite image obtained in step 3 provided the location and identity of each macrocycle/target pair. In step 4, we overlay the chip with wash buffer, zoom in on the brightest spots, and observe the fluorescence lifetime of each. Correcting for photobleaching (by having a reference spot on the side of the chip), the lifetime is inversely proportional to the dissociation rate, and thus a direct measure of affinity. This step can be carried out repeatedly and even after storing the chip. Beads and macrocycles can be dried and safely stored.

In a specific example, a library of DNA-encoded macrocycles has been hybridized to complementary sequences on beads in the wells of an Ion Torrent sequencing chip. Fluorescently labeled Src kinase (target) is flowed over the beads (macrocycles) in the wells of the Ion Torrent sequencing chip. Binding buffer is used for this binding reaction. Specific binding occurs between the target and some of the beads (macrocycles). The chip is then washed with wash buffer to remove unbound Src kinase. The beads with fluorescently labeled target on them will emit fluorescence light. The fluorescence intensity of single beads can be observed under a fluorescence microscope; the fluorescence intensity I(t) can be determined from fluorescence images taken over time. Photobleaching can be corrected by imaging a spot of fixed fluorophores that are anchored to the substrate.

Example 5

Array Image Analysis to Identify Target-Bound Candidate Molecules

The analysis of the image stack after collection consists of several substeps:

1. Background Subtraction—in ImageJ or an image processing software program, select a region of interest, take the average, and subtract this value from each pixel of the image. It sometimes yields cleaner result to subtract a slighter higher amount ~20-25% than the background.

2. Stitching—using MosaicJ, a plugin for ImageJ, align several rows of images together (de-activate rotation capabilities and blending when stitching). Here you click and drag the overlapping regions of adjacent images together by hand for best results.

3. Identify target wells—using the template matching plugin for ImageJ called cv_Match. The goal here is to identify wells that were fluorescing enough to consider it as having "matched" the criterion for having a target bound to it. The criterion we use is to take a single representative image of a targeted bead. This is done by selecting an ROI around the well that is considered to be representative, and storing this ROI as a file. Another method we have used is to average multiple images of different wells that are fluorescing, and use the average as the matching template. Then the cv_Match program will use this "template" image and your array image to match the pixel locations where the template matches the image in that region according to a threshold. The cv_Match program allows the user to select 6 different methods for determining matches between the template and data images. The method used in the results reported here is called the normalized cross-correlation method. The threshold for a match needs to be user adjusted for best results. Typical values for this will be 0.1-0.2, and will depend on the stringency of the filter you are interested in applying. The final output of the template matching program is a list of the pixel coordinates of the center point of matches to the template in the data image. After converting the pixel locations to well addresses, we can run Matlab programs that we wrote to extract the sequences corresponding to these addresses.

Example 6

NGS-Based Selection of Nucleic Acid Aptamers

This example involves a simple series of general protocol steps for selecting candidate molecules from designed, randomized and/or combinatorial libraries of nucleotide-containing oligomers comprising sequence and/or shape libraries through use of spatially addressable sequencing arrays. The essence of the underlying methodology is to sequence a library of oligos and expose these oligos on the array to a detectable target molecule or substance. The target can be a protein, peptide, or synthetic chemical. The outcome is a set of aptamer sequences that bind to the target and optionally a determination of how long and how tightly the selected aptamers bind to the target. Commercial applications include a) selection of aptamer-based drug candidates specific for therapeutic targets such as cell surface receptors, viruses, bacteria, modulators of immune and inflammatory function and signaling molecules involved in intercellular communication, b) selection of aptamer ligands against diagnostic analytes for clinical, environmental, agricultural, veterinary, industrial process control and military use, where analytes include, e.g., cardiac markers, cancer markers, serum proteins, immunoglobulins, hormones, vitamins, pollutants, toxins, prion proteins, precursors and products of bioreactors and large-scale chemical, and c) discovery of chemical genetic probes for unraveling intracellular signaling pathways in health and disease.

Aptamers (from Latin aptus: fitted, fastened) are oligonucleotides (oligos), typically about 10 to 100 bases in length, that bind targets with high affinity and specificity. Target-specific binding is due to the three-dimensional structure of these folded molecules, which, in turn, is dictated by the oligo sequence. Since they were first described in 1990, hundreds of aptamers have been identified that bind to a variety of targets such as proteins, peptides, toxins, dyes, coenzymes, vitamins and other organic and inorganic compounds. In the last few years it has become apparent that they may have many useful applications. Aptamers can be conveniently labeled, conjugated and immobilized through site-directed chemistries due to their relatively small size and defined chemical and sequence composition.

These well-defined, synthetic molecules (as opposed to purified biologicals) are amenable to reproducible, scalable and cost-effective production through established solid-phase synthesis techniques. They are good candidates for use as specific binding reagents in proteomic arrays, biosensors and bioMEMS devices and show promise for a wide variety of applications in drug discovery, diagnostics, medical devices and biopharmaceuticals. The first aptamer-based drug, Macugen, was launched in 2005 for the treatment of macular degeneration, and several others are in various stages of clinical trials. Aptamers are especially well suited for the site-specific labeling and conjugation required to develop homogeneous (mix and read) "aptamer beacon" assays.

Sequence-tagged aptamers can be immobilized in an addressable manner to form ordered molecular arrays. They can also be used to prepare well-defined bispecific or multispecific reagents in a modular, combinatorial fashion to detect or modulate molecular interactions. It has been suggested that epidermal growth factor receptors (EGFR)-specific ligands may be more effective when used in combination with other targeted therapies, in essence attacking different molecular targets simultaneously. Moreover, aptamers may be protected against nuclease attack (in vivo applications), by using mono- or dithiophosphate-backbone modified oligonucleotides. Such a "thioaptamer" against the RNase H domain of HIV-1 reverse transcriptase was stable against nuclease degradation and had a binding constant of 70 nM. It was also highly specific as it did not bind to E. coli RNase II.

Potentially attractive properties of aptamers for the molecular analysis of cancer include:

1. High specificity. Aptamers can distinguish (different binding constants) between closely related molecules such as protein kinase C isozymes having 96% homology, ATP and deoxy-ATP, NAD and NADH, and (iv) theophylline and caffeine, which differ by only a single methyl group.

2. Size. It has recently been shown that biotherapeutic molecules in the 100,000 Dalton range may yield optimal pharmacokinetic properties for cancer. Aptamers are typically in the 5,000-20,000 Dalton size range and may therefore be evaluated either as relatively low molecular weight biomimetics or, alternatively, formulated as multivalent chimera or conjugated to inexpensive carriers to assess bioavailability as a function of molecular size.

3. Low cost. Oligonucleotide synthesis has become a commodity service. Once the sequence is known, aptamers can be synthesized at greater than micromole scale for less than $0.50 per base.

4. Purity and lot-to-lot consistency. An aptamer is a well-characterized composition made up of a defined sequence of nucleotides. Labeled aptamers are conveniently prepared as pure, homogeneous, precisely defined reagents with known composition and specific activity, unlike antibody conjugates, which are typically heterogeneous.

5. Sourcing. Because oligos are routinely produced by automated synthesis, large-scale production can be scheduled on a just-in-time basis without the risks or uncertainties of biological production and sourcing.

6. Site-directed modification. Defined sequence and ready availability of nucleotide analogs allow many choices regarding designer labeling, including multiple, different labels per sequence.

7. Molecular sensing. Conformational changes on analyte binding combined with site-directed placement of effectors (e.g., fluorophores & quenchers) can conceivably be used to design analyte-dependent signal-generation into labeled aptamers. Also, allosteric molecular switches can be designed wherein binding at one sequence segment influences the activity of a label attached to a different sequence segment. Stimulus-responsive molecular switches for "mix and read" molecular sensing eliminate the need for time-consuming separation and wash steps in specific binding assays. Analyte-sensitive molecular sensors of this type are difficult to engineer with complex biological macromolecules such as antibodies.

8. Controlled immobilization. Unlike antibodies, oligos can be conveniently attached to surfaces through covalent attachment of the 3' or 5' end or any specified internal position of the sequence. Recognition of "immunologic blind spots." Aptamers may be selected to recognize analytes not amenable to hybridoma technology, e.g., toxic, small, and/or nonimmunogenic molecules or epitopes.

9. Stability. Nuclease-resistant aptamers can be designed with stability properties closer to benchtop chemicals than most biopolymers, which are prone to denaturation and/or aggregation under extreme conditions. Aptamers are synthetic polymers that are quite stable to ambient conditions, allowing them to be stored, handled and shipped much like benchtop chemicals. Whereas antibodies are temperature-sensitive proteins, aptamers are much more forgiving to transient or prolonged exposure to elevated temperatures.

10. Amplification. Aptamers can be replicated exponentially by nucleic acid amplification, presenting opportunities for high sensitivity assay formats that are implausible with nonamplifiable binding partners.

11. Self-assembly. Aptamers can be designed with hybridizable sequence segments for programmable, template-directed assembly of multifunctional reagents and/or convenient affinity-based attachment to oligo-modified surfaces.

12. Utility in proteomic arrays. Oligos offer a more stable, controllable molecular medium than immobilized antibodies for high-density arrays useful in drug discovery and proteomic applications. Also, oligo chemistry is more compatible with optical and electrochemical sensor technologies than protein-based recognition such as antibodies or cloned receptors.

13. Animal rights-friendly. Consistent with the growing international movement to minimize use of animals in medical testing and even monoclonal antibody production, aptamer selection and production does not require use of animals.

14. Automation. The NGS-based aptamer selection methods and devices described herein are readily amenable to automation and parallel processing.

Aptamer Selection Methods.

At present, aptamers are most often selected by a technique referred to as Systematic Evolution of Ligands by Exponential Enrichment (SELEX). In a typical SELEX selection experiment, target molecules are exposed to a large pool of randomized oligos (~$10^{14}$ molecules). Target-bound oligos are separated from the reaction mixture and PCR-amplified, resulting in an enriched pool of oligos. This pool is used for the next cycle of SELEX and through successive rounds of this process (typically 6-12 rounds) a highly enriched pool of candidate oligos is evolved. This enriched pool contains a heterogeneous population of oligos that may vary, for example, in nucleotide sequence, target specificity, binding affinity and amplification efficiency. These oligos are then cloned and sequenced to allow analytical and functional characterization of defined-sequence oligos. Candidate oligos determined to bind target molecules with measurable affinity and specificity are referred to as aptamers. Although the effectiveness of this method is well-demonstrated it has several serious drawbacks: i) it can be tedious, labor-intensive and time-consuming, as it requires repeated cycles of partitioning and amplification; ii) aptamer identification (sequencing) cannot be accomplished until the final cycle is complete; and iii) much time is invested before the success of selection is known; and if selected oligos are found to be false positives, the process must be restarted with little understanding of what went wrong—the method is largely a black box.

In this example, a library of DNA molecules having a 20-mer region of randomized bases flanked by adaptor sequence segments designed for HiSeq is sequenced according to the manufacturer's protocol (Illumina, Inc., San Diego, Calif.) The sequencing device is then washed with target-binding buffer. Purified, fluorescently labeled target protein (thrombin; Sigma Chemical Company, St. Louis, Mo.) is added to the chip following by washing in assay buffer. Fluorescence signal of labeled thrombin bound to candidate sequences is detected by fluorescence microscopy. The locations of fluorescently labeled polonies of single-sequence library candidates are then correlated with spatially addressed sequencing data to identify thrombin-binding candidate molecules (DNA sequences) from the library of candidate sequences.

Example 7

Selection of Nucleotide-Encoded Small Molecules Using the SOLiD System

In this example, the SOLiD™ 4 System (Applied Biosystems, Menlo Park, Calif.). The Applied Biosystems SOLiD™ 4 System is a revolutionary genetic analysis platform that enables massively parallel sequencing of clonally-amplified DNA fragments linked to beads. The sequencing methodology is based on sequential ligation with dye-labeled oligonucleotides. The SOLiD™ 4 System enables researchers to obtain higher-quality genomes at lower cost without the purchase of a new instrument. With Applied Biosystems, researchers experience peace of mind.

The PacBio SOLiD™ system uses kits to construct fragment libraries for sequencing on the SOLiD™ System. The SOLiD™ Fragment Library Oligos contain oligonucleotide adaptors and primers for fragment library construction. The SOLiD™ Fragment Library Construction Kits contain the necessary components (enzymes, buffers) for fragment library construction and are used with the SOLiD™ Fragment Library Oligos. Each kit contains sufficient material for constructing 10 fragment libraries. These products are compatible with all versions of the SOLiD™ System.

The PacBio SOLiD™ 4 System system is designed for targeted sequencing and relies upon the following kits and reagents:

SOLiD™ Fragment Library Construction Kit with Size Selection Gels
SOLiD™ Fragment Library Oligos Kit
SOLiD™ Fragment Library Construction Reagents
SOLiD™ Fragment Library Construction Kit.

Targeted sequencing allows researchers to focus on specific areas of interest within the genome, increasing the cost-effectiveness of studies and the depth of coverage. One common use of targeted sequencing is single nucleotide polymorphism (SNP) detection and validation, where the ability to accurately identify true SNPs and distinguish them from false positives is extremely important. Single molecule resolution allows comprehensive characterization of heterogeneous samples and identification of variation invisible to multi-molecule sequencing technologies.

A library of oligos that is complementary to DNA-, PNA, RNA-, nucleic-acid-encoded molecules (e.g. encoded macrocycle molecules created by David Liu, Harvard), is first sequenced using the PacBio SOLiD™ 4 System. Nucleic acid-encoded small molecules are then hybridized to the sequenced oligos, and the hybridized encoded molecules are exposed to a detectable target, i.e., a target that is detectably labeled with a fluorescent reporter, e.g., TAMRA, FITC or Cy5. The target can be a protein, peptide, or chemical. The outcome is the identity of a set of small molecules that bind to the target, as detected by fluorescence intensity, and determination of how long and how tightly the small molecules bind to the cognate target, as assessed by sequential fluorescence measurements. Commercial applications include selection of small molecule drug candidates against therapeutic targets, including cell surface antigens, hormone receptors, neurotransmitter receptors, growth factor receptors, viral and bacterial genes and coat proteins and, given the membrane permeability of low molecular weight of synthetic organic drugs, intracellular signaling molecules, genomic DNA sequences, transcription factors and regulatory molecules involved in protein synthesis and post-translational modification.

Example 8

Analysis of Candidate Proteins and/or Peptides Based on Physical Properties

This example includes the following general steps: 1) Sequence a library of oligos that is complementary to coding sequences of nucleic-acid-encoded peptide or protein (e.g., mRNA-encoded proteins), 2) Hybridize the encoded peptides and/or proteins to the oligos on the array and 3)

Examine the hybridized peptides and/or proteins for desirable physical properties. The outcome is the discovery of candidate peptides and proteins with desired physical properties.

Another embodiment of the invention is where the tagged candidate chemicals are proteins or peptides, such that the overall geometry of the embodiment is: a spatially addressable array, a plurality of different oligomers operably connected to said spatially addressable array (where one example of the operable connection are microscopic beads as shown in FIG. 6), a tag sequence which is complementary to and is hybridized to each of said oligomers, and a protein or peptide that is operably connected to each of said tag sequences.

In this embodiment, the invention would be used to find and select interesting physical properties of the protein. For example, the "candidate chemicals" could be mutants of green fluorescent protein (GFP) and the embodiment would then display all the GFP mutants via the spatially addressable array such that the user of the embodiment could examine which GFP mutants had the desired property. When the desired physical property is observed (for example, the amount of fluorescent emission or the particular wavelength of the emission) the mutant responsible for this desired property can be identified.

The specific identity of the peptide or protein that is responsible for the desired property would be found in the same manner as in other embodiments of this invention: a tag sequence on each candidate chemical (in this embodiment, the chemical is actually a peptide or protein) corresponds to, via the rules of nucleotide complementarity, the oligomer at a particular location in the spatially addressable array. Since the user of this embodiment will employ next generation sequencing (NGS) to obtain the sequences at each location in the spatially addressable array, the location of where the desired physical property was observed will directly correlate with a specific sequence and thus a specific tagged peptide or protein. The one-to-one tagging of each protein variant ensures that the identity of the peptide or protein can be determined by identifying the tag sequence.

Example 9

Affinity-Based Selection of Peptide or Protein Variants

Sequence a library of oligos that is complementary to DNA-, PNA-, RNA-, nucleic-acid-encoded molecules (e.g. mRNA-encoded proteins), then hybridize the encoded molecules to the oligos on the array, and then expose the encoded molecules to a detectable target. The target can be a protein, peptide, or chemical. The outcome is the identity of a set of molecules (e.g. mRNA-encoded proteins) that can bind to the target, and determine how long and how tightly they bind.

This embodiment has the same geometry as in FIG. 6 and as described in the previous example (where GFP was used as a specific example), i.e. with peptides or proteins as the "candidate chemicals". The difference between this example and the previous example is that in the previous example a physical property is what a user of the embodiment would select, whereas in this further embodiment the interaction between the tagged proteins and some known external targets (other proteins, small molecules, etc.) is what a user of this embodiment would find and identify. For example, mutant versions of the anti-HER2 antibody Herceptin® (Genentech, So. San Francisco, Calif.) could each be linked to a unique tag sequence.

Herceptin is a treatment for cancer that binds with high affinity to proteins on the outside of cancer cells (for example, HER2, aka ErbB2). The ErbB (or HER) protein family, a key family of transmembrane receptors is frequently overexpressed and causal to the tumor phenotype in a number of tissues, especially breast. The ErbB family of receptors' consists of ErbB1, ErbB2, ErbB3 and ErbB4, also called HER1, HER2, HER3 and HER4. All four receptors share sequence homology, and all but ErbB3 are functional tyrosine kinases. Current literature uses the "HER" (human EGF receptor) and "ErbB" acronyms interchangeably; we will use HER and will call the family "HERx" The underlying mechanism for aberrant, enhanced growth signal in human tumors is due to overexpression of receptors by transcriptional up-regulation and gene amplification. HER2 is the most common family member to be overexpressed in tumors. About 30% of sporadic breast cancers significantly overexpress HER2, and this overexpression is associated with poorer prognosis. Overexpression of HER2 has also been observed in at least 20% of carcinomas of the bladder, colon, pancreas, ovary and prostate and is also associated with poor prognosis. Overexpression of HER1 is found in some glial, renal, colorectal, ovarian and breast tumors. HER3 is found overexpressed in breast, gastric, pancreatic and colon tumors. HER2 appears to have the central role in orchestrating growth signals through the formation of heterodimers with HER1, HER3 and HER4. Despite an extensive search for a direct ligand for HER2, no convincing candidate has emerged. Instead, it appears that when HER1, HER3 and HER4 bind ligands, HER2 is recruited as the preferred heterodimer partner and this receptor heterodimer complex is key in amplifying a tyrosine kinase mediated growth signal. This network of signaling may be even more complex as all six potential heterodimers can be detected in crosslinking studies. The higher expression of HER receptors commonly found in tumors could produce a combination of signals unique to the tumor state. This known dependency of the heterodimeric state required for tumor growth signals, and recent X-ray crystallography data showing that the extracellular region of HER2 is open to binding and is important in stabilizing heterodimer formation, suggests that there are exceptional opportunities for extracellular aptamer binding to potentially inhibit an array of HER2 tumor growth signals. Results from the previous development of monoclonal antibodies (mAbs) to HER family receptors prove this principle of growth signal interference. Panels of different monoclonal antibodies to the HER2 receptor showed diverse growth effects on tumors overexpressing HER2 as seen in tissue culture and similarly in athymic mouse xenograft models. Particularly intriguing is that certain HER2 mAbs inhibit growth, others induce apoptosis, and still others induce differentiation. A mAb that binds to the external region of HER2 has been shown to induce extensive apoptosis when delivered in vitro to HER2 overexpressing breast tumor cell lines. A humanized mAb to HER2, Herceptin, has received FDA approval for treatment of metastatic breast cancer and can lengthen the life expectancy by 50% among those patients who respond to the drug. Currently, in phase II clinical trials is Pertuzumab a recombinant, humanized mAb of 2C4 that binds the extracellular domain II of HER2 and is the first drug to inhibit growth signaling through blocking HER2 heterodimerization. Two mAbs to HER1, cetuximab and panitumumab, are currently in use in the clinic and have been FDA approved for metastatic colorectal cancer. However, response to these antibodies is inevitably lost and both metastatic breast cancer and colorectal cancer develop resistance to these treatments leading to nearly uniform fatality. Clearly, these mAbs are first generation drugs and offer avenues for improvement. It is likely that aptamers have different binding preferences than antibodies, and, thus, they target, unique therapeutically critical epitopes that mAbs cannot recognize. For example, heregulin signaling was inhibited by an aptamer that preferentially binds to the oligomeric form of HER3. In addition, the smaller size of aptamers may allow them to target a number of nearby epitopes on a single receptor with less steric hindrance than mAbs. Thus, aptamers may offer unique therapeutic opportunities. Several different mechanisms have been suggested to be the dominant cause of the antitumor response in successful mAb HER receptor antibody therapy. These mechanisms include: induction of down-regulation of the receptor, increase in rate of receptor turnover (which could down-regulate a heterodimer partner), inhibition of normal heterodimer formation, induction of apoptosis, inhibition of secretion of vascular endothelial growth factor, and induction of antibody-dependent cellular cytotoxicity. In all of these cases, aptamers can be selected and developed to exploit these prospective mechanisms.

In addition to their therapeutic potential, aptamers may offer a means to more accurately measure HERx receptor levels in tumor tissue. In the case of HER2, accurately quantifying levels of these receptors in breast tumor tissue has been shown to be important for therapeutic decisions and for prognostic indications. Measuring receptor levels in breast tumor tissue by the current state of the art of immunohistochemistry has been confused by diverse sensitivities of antibodies and by edge effect staining likely due to protein denaturation at the air/liquid interface. It is likely that these antibody inconsistencies have lead to different estimates of the frequency of HER2 overexpression in sporadic breast cancer in different studies. In fact, because of inconsistencies in immunostaining, FISH (fluorescent in situ hybridization) is recommended for detection of gene amplification of the HER2 gene in tumor tissue as a means of screening patients likely to respond to Herceptin. Immunostaining is a two to three step process in which the primary mAb first binds the tissue and then a secondary polyclonal antibody conjugated with a fluorescent label is used to detect the primary or alternatively a secondary antibody bound to peroxidase is used followed by a substrate timed reaction with diaminobenzidine to produce a brown stain precipitate. Because of a number of variables in these reagents and reactions including the time of staining, the sensitivity of immunostaining in the clinic can vary from lab to lab. Aptamers can offer a homogeneous ligand molecule, of higher labeling sensitivity (if end labeled with a quantum dot) that does not have hydrophobic regions that denature during the staining process. Aptamers could offer a more reliable and consistent measurement for receptor staining that would vary less from lab to lab. Sensitivity, specificity, stability reproducibility and precision will all improve with the development of well-characterized synthetic ligand aptamers.

This embodiment provides a means to select for a mutant of Herceptin that binds with even higher affinity by an embodiment with the geometry shown in FIG. 6 and by flowing fluorescently labeled HER2 as the target over the spatially addressable array. In this embodiment, the best Herceptin mutant is identified by looking for the location in the spatially addressable array that has the brightest, longest-lived fluorescent signal, due to the longest persistence of the largest amount of target.

Our initial targets are the extracellular domains (ECD) of the Human epidermal growth factor receptors (EGFR) HER2, HER3 and HER4 (collectively called HERx) which are implicated in the development and progression of several cancers. HERx proteins make good targets because 1.) Binding to these molecules may block or slow cancer progression as evidenced by the success of Herceptin, a humanized antibody that binds HER2. Herceptin, though effective, is very expensive and less homogeneous than a synthetic aptamer. A HER2-specific aptamer (appropriately protected against nuclease degradation) may reduce cost of therapy and improve its reliability. It can also be chemically modified during synthesis or through site-directed chemistry to append shape/charge modifiers or carrier molecules to optimize pharmacokinetic properties, as molecular size has been shown to be critical to effective capillary extravasion, extracellular diffusion and catabolic clearance.

Example 10

Nucleic Acid Ligand Selection by Sequential Sequencing

Structure and functional analysis of the properties of candidate chemicals that specifically bind to or interact with target molecules can be assessed in situ on sequencing arrays by structure probing, target binding, enzymatic activity, substrate, coenzyme- or cofactor-facilitated activity and the like. In one embodiment, sequenceable molecules are 1) sequenced, 2) probed for target-binding activity or target-altering effect and identified by data reduction and/or visualization methods that correlate the spatially addressable identity of a sequence of a candidate chemical. In other embodiments, the order of operations is altered in favor of preferred discrimination of binding-, effector- and/or signal generating interactions. For example, selection of candidate molecules from a diverse library of randomized or partially randomized fixed-length oligonucleotides disposed in a spatially addressable array can be achieved as follows. The array containing candidate oligonucleotides is first exposed to target molecules followed by sequencing, removal of target molecules and resequencing. The difference in sequences obtained in the presence and absence of target is then determined by comparison of sequencing and resequencing data. An observed difference for any given site in the sequencing array between oligonucleotide sequence length and/or composition in the presence and absence of target molecules indicates that there was an interaction between the candidate oligonucleotide in that site and the target molecule. Sequences that are truncated both before and after removal of target molecules, i.e., short-read sequences, indicate the possibility that corresponding sites on the array contain target molecules tightly or pseudoirreversibly bound to candidate oligonucleotides. Further probing of these sites, e.g., using labeled anti-target antibodies, can be used to confirm the presence of oligonucleotide-target complexes.

Example 11

Label-Free Selection of Target-Binding Candidate Chemicals

In some embodiments, the binding and/or interaction of sequenced or sequenceable candidate chemicals with target molecules is detected in a label-free manner so as to allow selection of candidate ligands against unmodified target molecules. Selection against unlabeled targets is important, for example, in cases where suitable labels are not readily available and/or where labeling of the target molecule alters the recognition properties, binding sites or epitopes of the target molecule. Cases in which suitable labels are not readily available include, for example, detecting the binding of protein targets to candidate chemicals through use of labeled target-binding reagents such as labeled anti-target ligands (e.g., anti-target antibodies) or a combination of unlabeled target-binding ligands (e.g., antibodies) plus labeled secondary (anti-ligand or anti-antibody) antibodies. Although antibodies are widely available for thousands of biologically and/or commercially important targets, they are often unavailable for newly discovered targets. In addition, antibody-binding epitopes on target molecules may be unavailable for binding when the target molecule is tightly bound to a cognate ligand such as a newly discovered target-binding candidate chemical. Direct labeling of target molecules, e.g., through covalent attachment of dyes, fluorophores, enzymes and the like can provide sensitive detection of ligand-target complexes, but the need to covalently modify target molecules introduces additional steps, cost and can increase the heterogeneity of target preparations, nonspecific binding and associated uncertainty regarding the specificity of selected ligands for native binding sites on target molecules, particularly complex targets, e.g., proteins, for which site-directed labeling is nontrivial.

In one embodiment of the invention, short-read sequences serves as an indicator of tight binding between a target molecule and a cognate region of a sequenceable molecule, because sequencing is stopped, interrupted or skipped in the region of a target-ligand complex (as described in Example 5 above).

In another embodiment, candidate chemical binding to a target molecule interferes with the signal-generating mechanism of the sequencing reaction, e.g., the generation of photons or proton accompanying the addition or cleavage of nucleotides.

In the present example, label-free detection is achieved by capitalizing on candidate ligand modulation of an intrinsic signal-generating property of the target molecule, as illustrated here by inhibition and/or enhancement of the catalytic activity of a target enzyme, e.g., a phosphatase or tyrosine kinase.

Protein kinases and phosphatases are implicated in a variety of cellular processes such as proliferation, differentiation and apoptosis. Over one third of the proteins in the human proteome are phosphoproteins, and the families of protein kinases and phosphatases represent up to 5% of the human genome. These enzymes increase or suppress the activity of other enzymes, mark proteins for destruction, allow proteins to move from one subcellular compartment to another, or enhance or impede protein-protein interactions. Any change in the level, activity, or localization of these enzymes greatly influences the regulation of key processes. Because of the role that protein kinases and phosphatases play in cellular functions, they represent important drug targets.

The search for orally active protein kinase inhibitors proved successful with the FDA approval of STI-571 (Gleevec), a c-Abl tyrosine kinase inhibitor, to treat chronic myelogenous leukemia and the approval in Japan of Fasudil, a Rho kinase inhibitor, to treat cerebral vasospasm. Because of the promise of these enzymes as therapeutic targets, assay systems have been developed to monitor the activity of these enzymes under a variety of experimental conditions and to develop selective inhibitors of these enzymes for therapeutic applications. The ProFluor™ Src-Family Kinase Assay and the ProFluor™ Tyrosine Phosphatase Assay (Promega Corp., Madison Wis.) were designed to meet this need.

Baseline enzymatic activity(ies) of target enzyme molecules, in this case tyrosine kinase, are first determined on sequencing devices (in this case Illumina MySeq chips) using the Promega ProFluor Src-Family Kinase Assay (Promega Corp., Madison, Wis.). Nanomolar to micromolar concentrations of Src tyrosine kinase (Creative BioMart, Shirley, N.Y.) are titrated for signal-to-noise ratio in a 3×3 matrix of enzyme×substrate concentrations using the fluorogenic tyrosine kinase substrate Rhodamine 110 (Promega) according to Promega's instructions for 384 wells adapted to volumes and concentrations empirically determined for Illumina sequencing chips. Co-titration of enzyme/substrate concentrations are designed to determine appropriate reagent concentrations to yield approximately 5-50% of maximal (zero order) enzyme activity, preferably about 5-10% of maximum to simulate the likely amount of enzyme bound to candidate molecules during the target binding step.

Following baseline enzyme activity determination across the multiplicity of sites on the sequencing array, the array is washed to remove target enzyme, substrate and accessory reagents. The candidate chemical library is then dispensed to the sequencing chip, and candidate chemicals are sequenced according to the manufacturer (Illumina) protocol. After sequencing of candidate chemicals, target enzyme is added to the chip and incubated for 5-60 minutes, after which fluorogenic substrate is added to determine tyrosine kinase activity in each site on the spatially addressable array. Enzyme activity in each candidate molecule-exposed site is then compared with baseline enzyme activity to determine whether enzyme activity is inhibited, unchanged and/or accentuated by potential interaction with candidate chemicals.

Example 12

NGS-Based Selection of Nucleic Acids with Secondary Structure

Aptamers are short strands of DNA, RNA or other nucleic acids that fold into a three dimensional shapes. They represent a rapidly emerging class of promising molecules for diagnostic, therapeutic and research use. They have been used for targeted payload delivery into cancer cells and targeted tumor cell lysis. Aptamer AS1411 is in phase II clinical trials for myeloid leukemia and renal cell carcinoma. Due to their biocompatibility and easy handling, they are also optimal candidates for functionalizing therapeutic nanoparticles or carbon nanotubes for targeted delivery and targeted cancer heat therapy.

Aptamers derive their specific target binding properties from the enormous diversity of three-dimensional shapes formed by short DNA and RNA molecules. These shapes include hairpins, pseudoknots, quadruplexes, and bulges that fit tightly into conformational features of target molecules (e.g., cancer markers). The current technology for aptamer discovery, termed SELEX, is time-, labor-, material- and cost-intensive, since it involves many iterative steps of binding, washing, eluting and subsequent affinity tests. It also has potential "blind spots" due to selection bias that can result from differential amplification efficiencies and rates of candidate sequences that fold into secondary or tertiary structures resistant to amplification enzymes (e.g., polymerases and transcriptases).

In short, traditional SELEX methods are used to evolve subpopulations of candidate sequences through multiple successive rounds of affinity partitioning and amplification. The process does not directly detect the binding of a defined sequence to its cognate target, nor does it directly identify the sequence of a candidate nucleic acid molecule bound to its target. Rather, the SELEX process yields a pool of candidate molecules whose average affinity is greatly enhanced over the starting library. This evolved pool of candidate molecules is then subcloned into plasmids to create clones of individual aptamer candidates that can then be sequenced. Sequence alignment programs are then used to identify consensus sequences among the different candidates. These consensus sequences are then synthesized and tested individually for target binding properties. Thus, the SELEX process itself does not provide direct detection of clonal target-binding nucleic acid molecules during the selection process, nor does it provide direct sequence information for nucleic acid molecules specifically bound to their cognate targets. Identification and characterization of sequences within an evolved pool of candidates requires downstream cloning, sequencing, synthesis and testing of individual compounds from the evolved pool.

Application of Next-Generation Sequencing (NGS) to aptamer selection is dramatically simpler, more direct and less subject to processing biases and blind spots. This approach eliminates the costly iterative steps in SELEX, and it allows direct, in situ determination of target-binding sequences and their corresponding affinities as well as the influence of ligand binding on the functional activity of the target molecule. Direct detection and identification of target-binding sequences eliminates the need for offline subcloning, sequencing and inference-based deconvolution of candidate sequences.

Embodiments of the present invention reduce uncertainty due to amplification-based biases, blind spots and inference-based methods of deconvoluting candidate sequences through direct, on-chip analysis of candidate sequences and their target-binding properties. To demonstrate that our NGS-based aptamer selection method can be performed on candidate nucleic acid sequences containing regions of secondary structure that might introduce sequencing artifacts, e.g., stops, pauses, short-reads or base skipping, we initially focused on sequencing variants of the quadruplex-based thrombin aptamer (GGTTGGTGTGGTTGG, SEQ ID NO:1) using the Ion Torrent PGM (Life Technologies, Grand Island, N.Y.) as a model system. The highly stable quadruplex motif of this aptamer represents an ideal test case for addressing potential structural blind spots. We obtained DNA libraries containing a 20mer GT randomer region flanked by Ion Torrent adaptor sequences (ITD, Coralville, Iowa). Libraries were doped with increasing amounts of the thrombin aptamer (with adaptors). Sequencing according to the manufacturer's instructions provides full-length reads of the thrombin aptamer and its GT variants, indicating that the quadruplex motif does not interfere with sequencing. Exposure of sequencing chips to TAMRA-labeled thrombin followed by washing and fluorescence imaging shows that the highest intensity and residence time of the TAMRA signal occurs in wells containing the full-length thrombin binding quadruplex (GGTTGGTGTGGTTGG, SEQ ID NO:1) with less intense signals in wells containing closely-related variants. The number of full-length reads correlates with the amount of thrombin aptamer doped into GT randomer libraries. By demonstrating the ability to sequence quadruplex-containing oligonucleotide libraries and to identify thrombin-binding aptamers in situ on Ion Torrent sequencing chips followed by direct assessment of labeled thrombin binding, we are now able to apply this technology to nucleotide and nucleotide-encoded library selection for other target binding ligands with a degree of confidence that ligand selection can be performed even with libraries enriched in sequences containing stable secondary structure.

Example 13

NGS-Based Selection of Small Molecule

Target-Binding Ligands Using 454 Sequencing

Revenue growth and market capitalization of pharmaceutical firms have plunged over the past 10 years. Why? An important factor is that the engine for growth in drug discovery has come to a standstill. Historic reliance on synthetic organic chemistry and more recent innovations in combinatorial chemistry, randomer libraries and high-throughput screening have individually and collectively failed to meet expectations, as measured by the annual number of new drug approvals. These more recent innovations have yet to be validated in the marketplace, and the cost of conventional block-and-tackle drug development has begun to outweigh returns.

Two of the most substantial areas of venture capital/private equity investment in life sciences over the past five years include biomedical applications of nanotechnology and next-generation sequencing (NGS). Investment in NGS is rapidly shifting from technology development to new applications. Until recently, the universal goal of NGS was rapid whole genome sequencing (<$1000/genome). We believe we are the first to use NGS for cancer drug discovery using synthetic nucleic acid and nucleotide-encoded chemical libraries.

454 Sequencing (454 Life Sciences Corp., A Roche Company, Branford, Conn.) is a Next-Generation Sequencing, or NGS technology through which data is generated using pyrosequencing chemistry where clonally amplified libraries are sequenced by synthesis. Libraries are prepared using emulsion-based PCR (emPCR) amplification on beads. Each bead occupies a well on a Pico-Titer-Plate or PTP plate and the nucleotides in the sequence are determined by a chemiluminescent signal occurring during nucleotide incorporation. This signal is captured by a high resolution camera and is proportional to the number of nucleotides incorporated. The signals are processed and sequence is determined. With the GS Junior system used here, a single instrument run produces up to 1 million sequence reads for libraries averaging 400 bp and can be adapted for short read (>200 bp), as applied in this example.

When amplicon libraries are <200 bp, the normal conditions for emPCR amplification may result in excess amplification. An excess of sequencing templates on the DNA beads can cause an increased consumption of nucleotides during the sequencing run which may result in incomplete extension events; also, the increased signal may result in light scattering into nearby wells (well crosstalk) and cause their elimination due to signal processing filtering. To prevent this, the emPCR amplification procedure is modified for short sequence libraries such that the amount of Amp Primer (A or B) is reduced by 75% in the Live Amp Mix (and this volume replaced with molecular biology grade water). We use here the Lib-A method and adjust the Live Amp Mix volume from 40 ul to 10 ul for use on the GS Junior and compensate the volume reduction with molecular biology grade water.

This example focuses on NGS as a high-throughput way to decode single-sequence-per-bead DNA-encoded libraries. Micron-sized beads arrayed in millions of microelectronic wells are used to simultaneously sequence and then functionally select candidate molecules. The approach combines programmable DNA-encoded macrocycle synthesis, Lab-on-Bead processing and NGS to identify new ligands that modulate tyrosine kinase signaling (e.g., cytoplasmic Src kinase) by members of the erbB family of receptors (e.g., Her2) that are overexpressed in breast, prostate and ovarian cancers. Synthetic macrocycles represent an attractive class of drug candidates compared to their linear counterparts in terms of potency, solubility, lipophilicity, specificity, multivalent binding, metabolic stability, bioavailability and membrane permeability. To date, most of the >100 approved macrocycle drugs are derived or modified from natural sources rather than de novo synthesis. Massively parallel macrocycle synthesis can now be achieved by DNA templating, each macrocycle created with a DNA tag that both directs synthesis and encodes candidate identity. The bottleneck in encoded library-based discovery is the need for rapid, efficient screening and selection methods to reduce cost, time, labor and required amounts of library and target. Next-generation sequencing (NGS) machines use massively parallel sequencing of fragmented DNA to achieve throughputs up to about $10^8$ bases per run. Here, we use the 454 GS Junior to test a promising, but significantly underexplored class of DNA-tagged macrocycles for binding to the target Src kinase, implicated in a number of human cancers. The potency, specificity, affinity, multivalent binding, solubility, lipophilicity, membrane permeability, metabolic stability, and bioavailability of synthetic macrocycles are all significantly better than their linear counterparts, but their synthesis and screening have been challenging. NGS sequencing is used in this example to provide spatially addressable bead-based sequence reads using a medium-sized DNA-encoded macrocycle library (provided by our collaborator, David Liu, Harvard University, Boston, Mass.) that has been validated against our target of interest, Src kinase.

Demonstrated herein is technical feasibility of our superior NextGen Lab-on-Bead™ technology by using our NextGen Lab-on-Bead™ technology to select ligands against the clinically important Src kinase from a 13,824 member DNA-encoded macrocycle library, which contains known Src kinase-binding ligands. The goal of this demonstration is identification of approximately 100 target-binding sequences, over 80% or which are verified ligands; that is, a previously discovered ligand or a newly discovered ligand with $k_d$<$10^{-2}$ s$^{-1}$.

Synthetic Macrocycles. Macrocycles are ring structures consisting of dozens of atoms. Among over 100 macrocycle drugs currently on the market, the majority are derived from natural sources such as microbes and plants. Synthetic macrocycles represent an extremely promising, yet significantly underexploited class of small molecules for new drug discovery. They mimic natural products, and their circular, rather than linear, structure gives them several advantages for use as drugs. For example, they show profoundly increased pharmacological activity, which has been harnessed in the development of a range of naturally sourced drugs. They also have better specificity, affinity, multivalent binding, solubility, lipophilicity, membrane permeability, metabolic stability, and bioavailability.

Current Selection and Screening. Currently, such libraries are screened by SELEX-type approaches, in which the encoded macrocycles are iteratively bound to a target, washed, eluted, and bound again. Disadvantages include the required investment of time and labor, use of significant amounts of precious library material, and the need to subclone selected sequences. Further, these approaches are frequently unsuccessful, and detecting exactly which step failed is difficult. In a better approach, each binder would be identified in a single cycle, without iterations and without subcloning. Finally, binding affinity cannot be determined until the entire screening process has been completed. A better approach would provide the affinity for each molecule during the selection process.

This approach provides, in some embodiments, the following advantages over current SELEX-based and other drug discovery methods.

1. It is a single-round selection method and thus avoids iterative selection cycles.
2. It uses less material (10 femtomoles of target and <100 femtomoles of a million member library).
3. It is less time- and labor-intensive, thanks to the massive parallelism of high-density NGS chips.
4. It uses a priori sequencing and, thus, eliminates subcloning, again saving time, labor and materials.
5. It is a combination of existing technologies. Thus, it is transferable and feasible.
6. It is versatile, as it can be used for both encoded molecules and aptamers—even those with backbones that prevent PCR (e.g., PNA).
7. It can accommodate multiple targets simultaneously by using targets or anti-target ligands labeled with distinct fluorophores. This feature also allows testing of synergistic or cooperative binding of targets.
8. It may be used to test target functionality (e.g., enzymatic activity) instead of only detecting target binding, provided target functionality involves release of ions (e.g., through catalytic activity).
9. It allows the in situ determination of binding affinities for each binder. A particularly attractive and unique feature of our method in that both the identity and the binding affinity of each binder are determined in a single run.
10. Target binding to a specific macrocycle is detected on single beads that sequenced by the 454 GS Junior. Thus, the identity of each macrocycle is known immediately, without the need for iterative selection cycles or subcloning. The lifetime of each macrocycle-target pair can be determined on-chip.

Step 1) 454 Sequencing. Complementary sequences of each macrocycle's coding DNA are attached to micron-scale beads using emulsion PCR (em-PCR) and sequenced using the GS Junior using the manufacture's protocol, The outcome of this sequencing is an array file that lists the sequences and well number for each bead; i.e., the sequence and position of each bead are known. Moreover, in some embodiments, the chip can be used for decoding and analyzing library drug candidates, as outlined in steps 2-4.

Step 2) Macrocycle hybridization. The macrocycle library is hybridized to the beads localized in the GS Junior sequencing cartridge.

Step 3) Target binding. Target molecules are flowed across the substrate containing the beads with attached macrocycles, and significant binding results in a strong signal.

Step 4) Dissociation constant. After a wash step, we determine the lifetime, τ, of the signal in situ. τ is inversely proportional to the dissociation rate, $k_d$, and, thus, a measure of the affinity for each binding pair.

In essence, in this embodiment we are performing three post-sequencing steps on the DNA chip. In one run, we get the identity, target-binding properties and approximate dissociation rate of each of the best-binding macrocycles.

Examples 14-18

Additional Illustrative Embodiments

FIG. 7 is an electron micrograph of an ION TORRENT 314 spatially addressable FET array. The array contains approximately one million wells, forming approximately one million separate and discrete locations. Beads are deposited in some of the wells, which beads are fully gold coated and can be seen in the micrographic image.

FIG. 8 is an electron micrograph of a portion of an ION TORRENT 316 spatially addressable FET array. The array contains approximately six million wells, forming approximately six million separate and discrete locations. Beads are deposited in wells, which beads are partially gold coated, and can be seen in the micrographic image.

FIG. 9 is an electron micrograph of an ION TORRENT 318 spatially addressable FET array. The array contains approximately twelve million wells, forming approximately twelve million separate and discrete locations. Beads are deposited in some of the wells, which beads are fully gold coated, and can be seen in the micrographic image.

FIG. 10 is an electron micrograph of an ION PROTON I spatially addressable FET array. The array contains approximately 160 million wells, forming approximately 160 million separate and discrete locations. Beads are deposited in some of the wells, which beads are partially gold coated, and can be seen in the micrographic image.

FIG. 11 is a fluorescent micrograph image of an ION TORRENT 314 spatially addressable FET array like that shown in FIG. 11 above. Beads are deposited in some of the wells, which beads have an oligonucleotide coupled thereto. A complementary oligonucleotide that is labelled with a fluorescent dye is contacted to the array, the array then washed, and the array imaged with the fluorescent microscope. Beads to which the complementary oligonucleotide has hybridized fluoresce in the image.

The foregoing is illustrative of specific embodiments of the present invention, and is not to be construed as limiting thereof. The invention is defined by the following claims, with equivalents of the claims to be included therein.

We claim:

1. A sequencing device comprising:
   (a) a spatially addressable sequencing array, said array comprising a plurality of separate and discrete sequencing locations thereon, said separate and discrete sequencing locations contacted with at least one sequencing reagent;
   (b) a plurality of different oligomers operably connected to said spatially addressable sequencing array at different ones of said separate and discrete sequencing locations;
   (c) a tag sequence which is complementary to, and is hybridized to, each of said oligomers; and
   (d) a candidate chemical operably connected to each of said tag sequences,
   wherein each of said separate and discrete sequencing locations is a unique identifier for its corresponding oligomer
   and wherein said tag sequence is a unique identifier for its connected candidate chemical.

2. The sequencing device of claim 1, wherein said spatially addressable sequencing array is a field-effect transistor array, an electrochemical array or an optical array.

3. The sequencing device of claim 1, wherein said oligomers and said tag sequences are nucleic acids.

4. The sequencing device of claim 1, wherein said candidate chemicals are selected from the group consisting of small molecules, peptides, carbohydrates, lipids, monomers, polymers and conjugated molecules.

5. The sequencing device of claim 1, wherein said sequencing array comprises a substrate having a plurality of wells formed therein, said wells defining said plurality of separate and discrete sequencing locations,
   said sequencing device further comprising at least one particle deposited in each well of at least a subset of said plurality of wells, with said oligomers coupled to said particles.

6. A sequencing-based molecular discovery system comprising the sequencing device of claim 1 and at least one input apparatus.

7. The sequencing device of claim 1, wherein the sequencing reagent is selected from the group consisting of transcriptases, polymerases, deoxynucleoside triphosphates and oligonucleotide primers.

8. A sequencing device comprising:
   (a) a spatially addressable sequencing array, said sequencing array comprising a plurality of separate and discrete sequencing locations thereon, said separate and discrete sequencing locations contacted with at least one sequencing reagent;

SEQUENCE LISTING

<160> NUMBER OF SEQ ID NOS: 1

<210> SEQ ID NO 1
<211> LENGTH: 15
<212> TYPE: DNA
<213> ORGANISM: Artificial
<220> FEATURE:
<223> OTHER INFORMATION: Thrombin binding quadruplex sequence

<400> SEQUENCE: 1
ggttggtgtg gttgg                                                    15

(b) a plurality of different oligomers operably connected to said spatially addressable sequencing array at different ones of said separate and discrete sequencing locations; and (c) a detectably labeled nonnucleic acid target molecule noncovalently bound to at least one of said different oligomers, wherein each of said separate and discrete sequencing locations is a unique identifier for its corresponding oligomer.

9. The sequencing device of claim 8 wherein said nonnucleic acid target molecule comprises at least one of a protein, a peptide, a therapeutic target or a diagnostic analyte.

10. The sequencing device of claim 8, wherein said spatially addressable sequencing array is a field effect transistor array, an electrochemical array or an optical array.

11. The sequencing device of claim 8, wherein said oligomers are nucleic acids.

12. The sequencing device of claim 8, wherein said oligomers are selected from the group consisting of nucleotides, oligonucleotides and nonnaturally occurring nucleic acid molecules.

13. The sequencing device of claim 8, wherein said oligomers further comprise at least one of a tag sequence or a nonnucleic acid moiety.

14. The sequencing device of claim 8, wherein said sequencing array comprises a substrate having a plurality of wells formed therein, said wells defining said plurality of separate and discrete sequencing locations, said sequencing device further comprising at least one particle deposited in each well of at least a subset of said plurality of wells, with said oligomers coupled to said particles.

15. A sequencing-based molecular discovery system comprising the sequencing device of claim 8 and at least one input apparatus.

16. The sequencing device of claim 8, wherein the sequencing reagent is selected from the group consisting of transcriptases, polymerases, deoxynucleoside triphosphates and oligonucleotide primers.

* * * * *

UNITED STATES PATENT AND TRADEMARK OFFICE
CERTIFICATE OF CORRECTION

PATENT NO. : 10,481,153 B2
APPLICATION NO. : 15/654309
DATED : November 19, 2019
INVENTOR(S) : Bonin et al.

Page 1 of 1

It is certified that error appears in the above-identified patent and that said Letters Patent is hereby corrected as shown below:

In the Specification

Column 16, Line 16: Please correct "HiSeg™" to -- HiSeq™ --

Column 16, Line 17: Please correct "MiSeg™" to -- MiSeq™ --

Signed and Sealed this
Fifth Day of May, 2020

Andrei Iancu
*Director of the United States Patent and Trademark Office*